US011291426B2

(12) United States Patent
Behzadi

(10) Patent No.: US 11,291,426 B2
(45) Date of Patent: Apr. 5, 2022

(54) QUANTITATIVE ASSESSMENT OF IMPLANT BONE PREPARATION

(71) Applicant: Kambiz Behzadi, Pleasanton, CA (US)

(72) Inventor: Kambiz Behzadi, Pleasanton, CA (US)

(*) Notice: Subject to any disclaimer, the term of this patent is extended or adjusted under 35 U.S.C. 154(b) by 5 days.

(21) Appl. No.: 16/030,824

(22) Filed: Jul. 9, 2018

(65) Prior Publication Data

US 2019/0133547 A1 May 9, 2019

Related U.S. Application Data

(63) Continuation-in-part of application No. 16/030,603, filed on Jul. 9, 2018, which is a continuation-in-part
(Continued)

(51) Int. Cl.
*A61B 17/58* (2006.01)
*A61B 17/60* (2006.01)
*A61F 2/00* (2006.01)
*A61B 7/02* (2006.01)
*A61F 2/34* (2006.01)
(Continued)

(52) U.S. Cl.
CPC .............. *A61B 7/023* (2013.01); *A61B 9/00* (2013.01); *A61F 2/34* (2013.01); *A61F 2/468* (2013.01); *A61F 2/4609* (2013.01); *A61F 2/4657* (2013.01); *A61B 7/005* (2013.01); *A61B 2090/064* (2016.02); *A61B 2090/065* (2016.02); *A61F 2002/3456* (2013.01); *A61F 2002/469* (2013.01); *A61F 2002/4666* (2013.01); *A61F 2002/4681* (2013.01)

(58) Field of Classification Search
CPC combination set(s) only.
See application file for complete search history.

(56) References Cited

U.S. PATENT DOCUMENTS 1,455,621 A 5/1923 Joyner
2,121,193 A 6/1938 Hanicke
(Continued)

FOREIGN PATENT DOCUMENTS

| EP | 1433445 A1 | 6/2004 |
|---|---|---|
| WO | 2017029173 A1 | 2/2017 |
| WO | 2018031752 A1 | 2/2018 |

OTHER PUBLICATIONS

U.S. Appl. No. 16/030,603, filed Jul. 9, 2018, Kambiz Behzadi.
(Continued)

*Primary Examiner* — Sameh R Boles
(74) *Attorney, Agent, or Firm* — Patent Law Offices Michael E. Woods; Michael E. Woods

(57) ABSTRACT

A system and method for quantitatively assessing, during bone preparation, an estimation of future a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements.

25 Claims, 16 Drawing Sheets

Related U.S. Application Data of application No. 15/716,533, filed on Sep. 27, 2017, which is a continuation-in-part of application No. 15/687,324, filed on Aug. 25, 2017, said application No. 16/030,603 is a continuation-in-part of application No. 15/284,091, filed on Oct. 3, 2016, now Pat. No. 10,441,244, said application No. 15/716,533 is a continuation-in-part of application No. 15/284,091, filed on Oct. 3, 2016, now Pat. No. 10,441,244, said application No. 15/687,324 is a continuation of application No. 15/284,091, filed on Oct. 3, 2016, now Pat. No. 10,441,244, which is a continuation-in-part of application No. 15/234,782, filed on Aug. 11, 2016, said application No. 15/716,533 is a continuation-in-part of application No. 15/234,782, filed on Aug. 11, 2016, which is a continuation-in-part of application No. 15/202,434, filed on Jul. 5, 2016, said application No. 15/716,533 is a continuation-in-part of application No. 15/202,434, filed on Jul. 5, 2016.

(60) Provisional application No. 62/651,077, filed on Mar. 31, 2018, provisional application No. 62/355,657, filed on Jun. 28, 2016, provisional application No. 62/353,024, filed on Jun. 21, 2016, provisional application No. 62/277,294, filed on Jan. 11, 2016.

(51) Int. Cl.
　　*A61F 2/46*　　　(2006.01)
　　*A61B 9/00*　　　(2006.01)
　　*A61B 90/00*　　　(2016.01)
　　*A61B 7/00*　　　(2006.01)

(56) References Cited

U.S. PATENT DOCUMENTS

| | | |
|---|---|---|
| 3,818,514 A | 6/1974 | Clark |
| 4,135,517 A | 1/1979 | Reale |
| 4,457,306 A | 7/1984 | Borzone |
| 4,530,114 A | 7/1985 | Tepic |
| 4,712,951 A | 12/1987 | Brown |
| 5,108,400 A | 4/1992 | Appel et al. |
| 5,133,765 A | 7/1992 | Cuilleron |
| 5,318,570 A | 6/1994 | Hood et al. |
| 5,534,006 A | 7/1996 | Szabo et al. |
| 5,769,092 A | 6/1998 | Williamson, Jr. |
| 5,806,518 A | 9/1998 | Mittelstadt |
| 5,849,015 A | 12/1998 | Haywood et al. |
| 5,980,528 A | 11/1999 | Salys |
| 6,110,179 A | 8/2000 | Flivik et al. |
| 6,161,545 A | 12/2000 | Chow |
| 6,204,592 B1 | 3/2001 | Hur |
| 6,585,771 B1 | 7/2003 | Buttermilch et al. |
| 7,036,211 B1 | 5/2006 | Panks |
| 8,167,823 B2 | 5/2012 | Nycz et al. |
| 8,603,100 B2 | 12/2013 | Muller |
| 9,999,518 B2 | 6/2018 | Mani et al. |
| 10,251,663 B2 | 4/2019 | Behzadi |
| 2002/0183851 A1 | 12/2002 | Spiegelberg et al. |
| 2003/0065398 A1 | 4/2003 | Cueille et al. |
| 2003/0229357 A1 | 12/2003 | Dye |
| 2005/0101962 A1* | 5/2005 | Schwenke ............ A61F 2/4618 606/86 R |
| 2005/0154398 A1 | 7/2005 | Miniaci et al. |
| 2006/0015110 A1 | 1/2006 | Pepper |
| 2006/0142754 A1 | 6/2006 | Irion et al. |
| 2007/0005144 A1 | 1/2007 | Leisinger et al. |
| 2007/0162038 A1 | 7/2007 | Tuke |
| 2009/0192626 A1 | 7/2009 | Keefer et al. |
| 2010/0249796 A1 | 9/2010 | Nycz |
| 2011/0004318 A1 | 1/2011 | Tulkis et al. |
| 2011/0178521 A1 | 7/2011 | Siravo et al. |
| 2011/0264009 A1 | 10/2011 | Walter et al. |
| 2012/0172939 A1 | 7/2012 | Pedicini |
| 2012/0209277 A1 | 8/2012 | Leparmentier et al. |
| 2013/0204264 A1 | 8/2013 | Mani et al. |
| 2013/0211535 A1 | 8/2013 | Cueille |
| 2013/0226189 A1 | 8/2013 | Young |
| 2014/0135773 A1 | 5/2014 | Stein et al. |
| 2014/0135791 A1 | 5/2014 | Nikou et al. |
| 2015/0182350 A1 | 7/2015 | Behzadi |
| 2015/0182351 A1 | 7/2015 | Behzadi |
| 2015/0196343 A1 | 7/2015 | Donald et al. |
| 2015/0201918 A1 | 7/2015 | Kumar et al. |
| 2015/0282856 A1 | 10/2015 | Haiat et al. |
| 2016/0166390 A1 | 6/2016 | Dye et al. |
| 2016/0206430 A1 | 7/2016 | Grostefon et al. |
| 2016/0206433 A1 | 7/2016 | Grostefon et al. |
| 2016/0220315 A1 | 8/2016 | Falardeau et al. |
| 2017/0056205 A1 | 3/2017 | Biegun et al. |
| 2017/0196506 A1 | 7/2017 | Behzadi |
| 2017/0196701 A1 | 7/2017 | Behzadi et al. |
| 2017/0196704 A1 | 7/2017 | Behzadi et al. |
| 2017/0196705 A1 | 7/2017 | Behzadi |
| 2017/0196706 A1 | 7/2017 | Behzadi |
| 2017/0196707 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0325972 A1 | 11/2017 | Steif |
| 2017/0340456 A1 | 11/2017 | Behzadi |
| 2018/0049891 A1 | 2/2018 | Termanini |
| 2018/0235764 A1 | 8/2018 | Moore et al. |
| 2018/0235765 A1 | 8/2018 | Welker et al. |

OTHER PUBLICATIONS

U.S. Appl. No. 16/154,033, filed Oct. 8, 2018, Kambiz Behzadi et al.
U.S. Appl. No. 62/277,294, filed Jan. 11, 2016, Kambiz Behzadi.
U.S. Appl. No. 62/353,024, filed Jun. 21, 2016, Kambiz Behzadi.
U.S. Appl. No. 62/355,657, filed Jun. 28, 2016, Kambiz Behzadi.
U.S. Appl. No. 62/373,515, filed Aug. 11, 2016, Kambiz Behzadi.
U.S. Appl. No. 62/651,077, filed Mar. 31, 2018, Kambiz Behzadi.
U.S. Appl. No. 15/202,434, filed Jul. 5, 2016, Kambiz Behzadi.
U.S. Appl. No. 15/234,782, filed Aug. 11, 2016, Kambiz Behzadi et al.
U.S. Appl. No. 15/234,880, filed Aug. 11, 2016, Kambiz Behzadi et al.
U.S. Appl. No. 15/235,032, filed Aug. 11, 2016, Kambiz Behzadi et al.
U.S. Appl. No. 15/235,053, filed Aug. 11, 2016, Kambiz Behzadi.
U.S. Appl. No. 15/284,091, filed Oct. 3, 2016, Kambiz Behzadi.
U.S. Appl. No. 15/362,675, filed Nov. 28, 2016, Kambiz Behzadi.
U.S. Appl. No. 15/396,785, filed Jan. 2, 2017, Kambiz Behzadi et al.
U.S. Appl. No. 15/398,996, filed Jan. 5, 2017, Kambiz Behzadi.
U.S. Appl. No. 15/453,219, filed Mar. 8, 2017, Kambiz Behzadi.
U.S. Appl. No. 15/592,229, filed May 11, 2017, Kambiz Behzadi.
U.S. Appl. No. 15/687,324, filed Aug. 25, 2017, Kambiz Behzadi.
U.S. Appl. No. 15/716,529, filed Sep. 27, 2017, Kambiz Behzadi et al.
U.S. Appl. No. 15/716,533, filed Sep. 27, 2017, Kambiz Behzadi.
International Search Report for International application No. PCT/US2017/012753, dated May 5, 2017.
Written Opinion of the International Searching Authority for International application No. PCT/US2017/012753 dated May 5, 2017.
International Search Report for International application No. PCT/US2017/046261, dated Oct. 8, 2017.
Written Opinion of the International Searching Authority for International application No. PCT/US2017/046261, dated Oct. 8, 2017.
International Search Report for International application No. PCT/US2017/046261, dated Oct. 18, 2017.
Written Opinion of the International Searching Authority for International application No. PCT/US2017/046261, dated Oct. 18, 2017.

\* cited by examiner

QUANTITATIVE ASSESSMENT OF IMPLANT BONE PREPARATION

CROSS REFERENCE TO RELATED APPLICATIONS

This Application is a Continuation-in-part of application Ser. No. 16/030,603 filed on Jul. 9, 2018. Application Ser. No. 16/030,603 claims the benefit of U.S. Provisional Application 62/651,077 filed on Mar. 31, 2018. Application Ser. No. 16/030,603 is a Continuation-in-part of application Ser. No. 15/716,533 filed on Sep. 27, 2017. Application Ser. No. 15/716,533 is a Continuation-in-part of application Ser. No. 15/687,324 filed on Aug. 25, 2017. Application Ser. No. 15/687,324 is a Continuation of application Ser. No. 15/284,091 filed on Oct. 3, 2016. Application Ser. No. 15/284,091 is a Continuation-in-part of application Ser. No. 15/234,782 filed on Aug. 11, 2016. Application Ser. No. 15/234,782 is a Continuation-in-part of application Ser. No. 15/202,434 filed on Jul. 5, 2016. Application Ser. No. 15/202,434 claims the benefit of U.S. Provisional Application 62/277,294 filed on Jan. 11, 2016. Application Ser. No. 15/234,782 claims the benefit of U.S. Provisional Application 62/355,657 filed on Jun. 28, 2016. Application Ser. No. 15/234,782 claims the benefit of U.S. Provisional Application 62/353,024 filed on Jun. 21, 2016. Application Ser. No. 15/716,533 is a Continuation-in-part of application Ser. No. 15/284,091 filed on Oct. 3, 2016. Application Ser. No. 15/716,533 is a Continuation-in-part of application Ser. No. 15/234,782 filed on Aug. 11, 2016. Application Ser. No. 15/716,533 is a Continuation-in-part of application Ser. No. 15/202,434 filed on Jul. 5, 2016. Application Ser. No. 16/030,603 is a Continuation-in-part of application Ser. No. 15/284,091 filed on Oct. 3, 2016. This Application claims the benefit of U.S. Provisional Application 62/651,077 filed on Mar. 31, 2018. This Application is a Continuation-in-part of application Ser. No. 15/716,533 filed on Sep. 27, 2017. This Application is a Continuation-in-part of application Ser. No. 15/284,091 filed on Oct. 3, 2016. All these applications are hereby expressly incorporated by reference thereto in their entireties for all purposes.

FIELD OF THE INVENTION

The present invention relates generally to assessing a quality of a press-fit installation of a structure, and more specifically, but not exclusively, to quantitative assessment of prosthesis press-fit fixation into a bone cavity, for example, assessment of press-fit fixation of an acetabular cup into a prepared (e.g., relatively under-reamed acetabulum) bone cavity.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Initial stability of metal backed acetabular components is an important factor in an ultimate success of cement-less hip replacement surgery. The press fit technique, which involves impaction of an oversized (relative to a prepared cavity in an acetabulum) porous coated acetabular cup into an under-sized cavity (relative to the prosthesis to be installed) of bone produces primary stability through cavity deformation and frictional forces, and has shown excellent long term results. This press fit technique avoids use of screw fixation associated with risk of neurovascular injury, fretting and metallosis, and egress of particulate debris and osteolysis.

However, it has been difficult to assess a primary implant stability due to complex nature of bone-implant interface, or to evaluate an optimal press fit fixation. The initial interaction of the implant with bone is due the circumferential surface interference at the aperture transitioning to compression of the cavity with deeper insertion. A compromise exists between seating the cup enough to get sufficient primary stability and avoiding fracture of bone. There is no quantitative method in current clinical practice to assess the primary stability of the implant, with surgeons relying solely on their qualitative proprioceptive senses (tactile, auditory, and visual) to determine point of optimal press fit fixation.

Four factors associated with difficulty obtaining optimal press fit fixation: i) no current method exists to gauge the resulting stress field in bone during the impaction of an oversized implant; ii) the material properties of bone (bone density) vary significantly based on age and sex of the patient, and are unknown to the surgeon; iii) current mallet based techniques for impaction do not allow surgeons to control (quantify and increment) the magnitude of force using in installation; and iv) surgeons are charged with the difficult task of: a) applying and modulating magnitude of force; b) deciding when to stop application of force; and c) assessing a quality of press fit fixation all simultaneously in their "mind's eye" during the process of impaction.

A significance of this problem on patients, medical practice and economy is great. Although Total Hip Replacement (THR) is widely recognized as a successful operation, 3 to 25% of operations fail requiring revision surgery. Aseptic loosening of press fit THR components is one of the most common causes of failure at 50% to 90% and closely associated with insufficient initial fixation. Inadequate stabilization may lead to late presentation of aseptic loosening due to formation of fibrous tissue and over stuffing the prosthesis may lead to occult and/or frank peri-prosthetic fractures. The cost of poor initial press fit fixation resulting from (loosening, occult fractures, subsidence, fretting, metallosis, and infections) maybe under reported however estimated to be in tens of billions of dollars. Over 400,000 total hip replacements are done in US every year, over 80% of which are done by surgeons who do less than ten per year. The limitations of this procedure produce frustration and anxiety for surgeons, physical and emotional pain for patients, at great costs to society.

Initial implant fixation can be measured by pullout, lever out, and torsional test in vitro; however, these methods have minimal utility in a clinical setting in that they are destructive. Vibration analysis, where secure and loose implants can be distinguished by the differing frequency responses of the implant bone interface, has been successfully employed in evaluating fixation of dental implants however, this technology has not been easily transferable to THR surgery, and currently has no clinical utility.

In clinical practice, surgeons err on the side of not overstuffing the prosthesis which leads to a smaller under ream (or line to line ream) and screw fixation with attendant risks.

Finally, several visual tracking methods (Computer Navigation, Fluoroscopy, MAKO Robotics) are utilized to assess the depth of cup insertion during impaction in order to guide application of force; however, these techniques, from and engineering perspective, are considered to be open loop, where the feedback response to the surgeon is not a force (sensory) response, and therefore does not provide any information about the stress response of the cavity.

A system and method is needed to quantitatively assess a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

BRIEF SUMMARY OF THE INVENTION

Disclosed is a system and method for quantitatively assessing and estimating a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

The following summary of the invention is provided to facilitate an understanding of some of the technical features related to installation of an acetabular cup prosthesis into a relatively undersized prepared cavity in an acetabulum, and is not intended to be a full description of the present invention. A full appreciation of the various aspects of the invention can be gained by taking the entire specification, claims, drawings, and abstract as a whole. The present invention is applicable to other press fit fixation systems, including installation of different prostheses into different locations, and installation of other structures into an elastic substrate. Activities preparatory to the fixation, such as cavity or implant installation site preparation, may be used to parametrically or qualitatively estimate the pressfit fixation once the implant is actually installed. Some embodiments may model a bone preparation implement as or related to the implant. Some embodiments may be able to be used for both assessments of an estimate pressfit fixation during preparation and assessment of the pressfit fixation of the implant during installation—such as to help a surgeon improve/optimize bone preparation for an implant and efficient time. The surgeon may not stop too early or continue overly long during bone preparation.

Some embodiments of the proposed technology may enable a standardization of: a) application of force; and b) assessment of quality of fixation in joint replacement surgery, such that surgeons of all walks of life, whether they perform five or 500 hip replacements per year, will produce consistently superior/optimum/perfect results with respect to press fit fixation of implants in bone.

From the surgeon perspective this standardization process will level the playing field between the more and less experienced surgeons, leading to less stress and anxiety for the surgeons affecting their mental wellness. From the patient perspective there will be a decrease in the number of complications and ER admissions leading to decrease in morbidity and mortality. From an economic perspective there will be a significant cost savings for the government and insurance companies due to a decrease in the number of readmissions and revision surgery's, particularly since revision surgery in orthopedics accounts for up to 30% of a 50-billion-dollar industry.

To address this deficiency, some embodiments and related applications have considered a novel means of accessing and processing various force responses of bone (Invasive Sensing Mechanism) and propose that this mechanism can guide application of force to the bone cavity, to obtain optimal press fit technologically without reliance on surgeon's proprioception. There are several possible outcomes of this proposal, if validated, including that it may make joint replacement surgery a significantly safer operation leading to less morbidity and complications, readmissions, and revision surgery; resulting in great benefits to patients, surgeons and society in general.

An embodiment of the present invention may include a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level. Some embodiments may determine rigidity/elasticity from position, or vibration spectrum in air (sound) or bone. In some embodiments, while rigidity and elasticity may be determined in several different ways, some of which are disclosed herein, some implementations may determine a quantitative assessment responsive to evaluations of both responsive rigidity and elasticity factors during controlled operation of an insertion agency communicating an application force to a prosthesis (best fixation short of fracture—BFSF). BFSF may be related to one or both of these rigidity and elasticity factors.

An apparatus for insertion of a prosthesis into a cavity formed in a portion of bone, the prosthesis relatively oversized with respect to the cavity, including an insertion device providing an insertion agency to the prosthesis, the insertion agency operating over a period, the period including an initial prosthesis insertion act with the insertion device and a subsequent prosthesis insertion act with the insertion device; and a system physically coupled to the insertion device configured to provide a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

A method for an insertion of an implant into a cavity in a portion of bone, the cavity relatively undersized with respect to the implant, including a) providing, using a device, an implant insertion agency to the implant to transition the implant toward a deepen insertion into the cavity; and b) predicting, responsive to the implant insertion agency, a press-fit fixation of the implant at an interface between the implant and the cavity during the providing of the implant insertion agency.

An impact control method for installing an implant into a cavity in a portion of bone, the cavity relatively undersized with respect to the implant, including a) imparting a first initial known force to the implant; b) imparting a first subsequent known force to the implant, the first subsequent known force about equal to the first initial force; c) measuring, for each the imparted known force, an Xth number measured impact force; d) comparing the Xth measured impact force to the Xth−1 measured impact force against a predetermined threshold for a threshold test; and e) repeating steps b)-d) as long as the threshold test is negative.

A method for an automated installation of an implant into a cavity in a portion of bone, including a) initiating an application of an installation agency to the implant, the installation agency including an energy communicated to the implant moving the implant deeper into the cavity in response thereto; b) recording a set of measured response forces responsive to the installation agency; c) continuing applying and recording until a difference in successive measured responses is within a predetermined threshold to estimate no significant displacement of the implant at the energy as the implant is installed into the cavity; d) increasing the energy; e) repeating steps b)-c) until a plateau of the set of the measured response forces; and f) terminating steps b)-e) when a steady-state is detected.

A method for insertion of a prosthesis into a cavity formed in a portion of bone, the prosthesis relatively oversized with respect to the cavity, including a) applying an insertion agency to the prosthesis, the insertion agency operating over a period, the period including an initial prosthesis insertion act with the insertion device and a subsequent prosthesis insertion act with the insertion device; and b) providing a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An apparatus for installing a prosthesis into a relatively undersized prepared cavity in a portion of a bone, including a force applicator operating an insertion agency for installing the prosthesis into the cavity; a force transfer structure, coupled to the force applicator and to the prosthesis, for conveying an application force F1 to the prosthesis, the application force F1 derived from the insertion agency; a force sensing system determining a force response of the prosthesis at an interface of the prosthesis and the cavity, the force response responsive to the application force F1; and a controller, coupled to force applicator and to the force sensing system, the controller setting an operational parameter for the insertion agency, the operational parameter establishing the application force F1, the controller responsive to the force response to establish a set of parameters including one or more of a rigidity metric, an elasticity metric, and combinations thereof.

A method for installing a prosthesis into a relatively undersized cavity prepared in a portion of bone, including a) communicating an application force F1 to the prosthesis; b) monitoring a rigidity factor and an elasticity factor of the prosthesis within the cavity during application of the application force F1; c) repeating a)-b) until the rigidity factor meets a first predetermined goal; d) increasing, when the rigidity factor meets the predetermined goal, the application force F1; e) repeating a)-d) until the elasticity factor meets a second predetermined goal; and f) suspending a) when the elasticity factor meets the first goal and the rigidity factor meets the second goal.

An acetabular cup for a prepared cavity in a portion of bone, including a generally hemispherical exterior shell portion defining a generally hemispherical interior cavity; and a snubbed polar apex portion of the generally hemispherical exterior shell portion without degradation of the generally hemispherical interior cavity producing a polar gap within the prepared cavity when fully seated.

An implant for a prepared cavity in a portion of bone, including an exterior shell portion having an interior cavity; and a snubbed polar apex portion of the exterior shell portion without degradation of the interior cavity producing a polar gap within the prepared cavity when fully seated.

An apparatus for insertion of a prosthesis into a cavity formed in a portion of bone, the prosthesis relatively oversized with respect to the cavity, including means for applying an insertion agency to the prosthesis, the insertion agency operating over a period, the period including an initial prosthesis insertion act with the insertion device and a subsequent prosthesis insertion act with the insertion device; and means, physically coupled to the insertion device, for determining a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An apparatus for preparing a portion of bone for an insertion of a prosthesis, including a bone preparation device providing a bone preparation agency to the portion of bone using a bone preparation implement engaging the portion of bone, the preparation agency operating over a period, the period including an initial preparation act with the preparation device and a subsequent preparation act with the preparation device; and a system physically coupled to the preparation device configured to provide a parametric estimation of a pressfit fixation of the prosthesis to be installed into the portion of bone, the parametric estimation provided during the period, the parametric evaluation including an evaluation of a set of factors of the implement with respect to the portion of bone, the set of factors including one or more of a rigidity factor, an elasticity factor, and a combination of the rigidity factor and the elasticity factor.

A method for preparation of a cavity in a portion of bone for an insertion of a prosthesis, the cavity relatively undersized with respect to the prosthesis, including a) providing, using a device, a bone preparation agency to the portion of bone to form the cavity; and b) predicting, responsive to the bone preparation agency, a press-fit fixation of the prosthesis at an interface between the prosthesis and the cavity during the providing of the bone preparation agency.

An impact control method for preparing a portion of bone for installation of an implant into the portion of bone using a bone preparation implement engaging the portion of bone, including a) imparting a first initial known force to the implement; b) imparting a first subsequent known force to the implement, the first subsequent known force about equal to the first initial force; c) measuring, for each the imparted known force, an Xth number measured impact force; d) comparing the Xth measured impact force to the Xth−1 measured impact force against a predetermined threshold for a threshold test; and e) repeating steps b)-d) as long as the threshold test is negative.

A method for an automated bone preparation of a portion of bone using a bone preparation implement for an installation of an implant into the portion of bone, including a) initiating an application of a bone preparation agency to the implement, the preparation agency including an energy communicated to the implement moving the implement deeper into the bone in response thereto; b) recording a set of measured response forces responsive to the preparation agency; c) continuing applying and recording until a difference in successive measured responses is within a predetermined threshold to estimate no significant displacement of the implement at the energy as the implement is operated with respect to the portion of bone; d) increasing the energy; e) repeating steps b)-c) until a plateau of the set of the measured response forces; and f) terminating steps b)-e) when a steady-state is detected.

An apparatus for preparing a portion of bone using a bone preparation implement for installing a prosthesis into the portion of a bone, including a force applicator operating a bone preparation agency for preparing the portion of bone; a force transfer structure, coupled to the force applicator and to the implement, for conveying an application force F1 to the implement, the application force F1 derived from the preparation agency; a force sensing system determining a force response of the implement at an interface of the implement and the portion of bone, the force response responsive to the application force F1; and a controller, coupled to force applicator and to the force sensing system, the controller setting an operational parameter for the preparation agency, the operational parameter establishing the application force F1, the controller responsive to the force response to establish a set of parameters including one or more of a rigidity metric, an elasticity metric, and combinations thereof.

A method for preparing a portion of bone using a bone preparation implement for installing a prosthesis into the portion of a bone, including a) communicating an application force F1 to the implement; b) monitoring a rigidity factor and an elasticity factor of the implement within the portion of bone during application of the application force F1; c) repeating a)-b) until the rigidity factor meets a first predetermined goal; d) increasing, when the rigidity factor meets the predetermined goal, the application force F1; e) repeating a)-d) until the elasticity factor meets a second predetermined goal; and f) suspending a) when the elasticity factor meets the first goal and the rigidity factor meets the second goal.

An apparatus for preparing a portion of bone using a bone preparation implement for installing a prosthesis into the portion of a bone, including means for applying a bone preparation agency to the implement, the preparation agency operating over a period, the period including an initial preparation act with a bone preparation device and a subsequent preparation act with the bone preparation device; and means, physically coupled to the bone preparation device, for estimating a pressfit fixation of the prosthesis once installed into the portion of bone after preparation during the period, the estimation including an evaluation of a set of factors of the implement with respect to the portion of bone, the set of factors including one or more of a rigidity factor, an elasticity factor, and a combination of the rigidity factor and the elasticity factor.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 11 illustrates a comparison of F5 to F1;

FIG. 12 illustrates a comparison of ΔF5 to a predetermined threshold (e.g., 0.0);

FIG. 13 illustrates a comparison of F2 to F1;

FIG. 14 illustrates a comparison of ΔF2 to a predetermined threshold (e.g., 0.0);

DETAILED DESCRIPTION OF THE INVENTION

Figure 1:
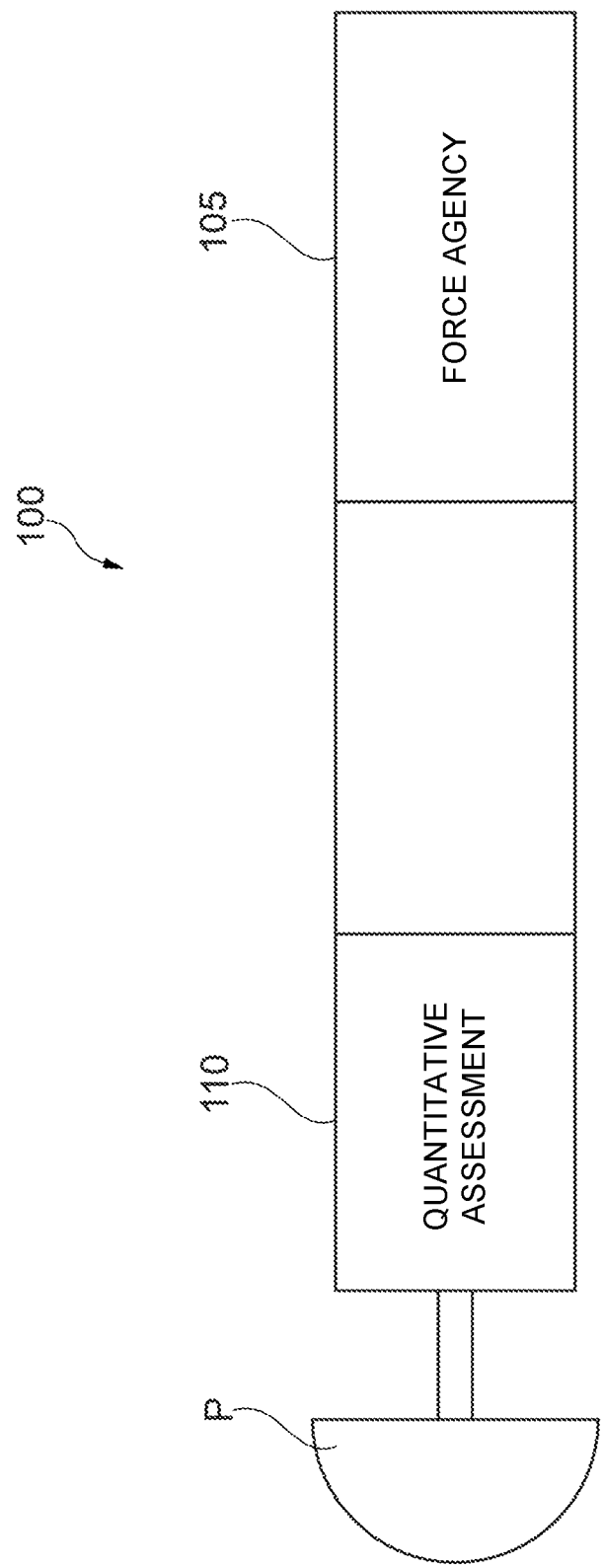
FIG. 1 illustrates an smart tool for prosthesis installation.

Embodiments of the present invention provide a system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, mallet or hammer refers to an orthopedic device made of stainless steel or other dense material having a weight generally a carpenter's hammer and a stonemason's lump hammer.

As used herein, an impact force for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs./square inch.

As used herein, the term "realtime" sensing means sensing relevant parameters (e.g., force, acceleration, vibration, acoustic, and the like) during processing (e.g., installation, reaming, cutting) without stopping or suspending processing for visual evaluation of insertion depth of a prosthesis into a prepared cavity.

The following description relates to improvements in a wide-range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

Embodiments of the present invention may include one of more solutions to the above problems. U.S. Pat. No. 9,168,154, expressly incorporated by reference thereto in its entirety for all purposes, includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a (hollow cylindrical mass) that travels over a stainless rod.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKO) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR, including examples of a device, which may be automated, for production and/or communication of an installation agency to a prosthesis.

FIG. 1 illustrates a smart tool 100 for prosthesis installation, including structures and methods for operation of a force agency 105 and a responsive quantitative assessment 110 with respect to installation of a prosthesis P (e.g., an acetabular cup) into a prepared cavity in a portion of bone (e.g., an acetabulum). Agency 105 may include several different types of force applicators, including vibratory insertion agencies and/or controlled impaction agencies and/ or constant applied force and/or other force profile as described in the incorporated patents and applications. Quantitative assessment 110 may include a processor and sensors for evaluating parameters and functions as described herein including a rigidity metric and an elasticity metric, for press-fit fixation of prosthesis P, such as in realtime or near-realtime operation of force agency 105.

Figure 2:
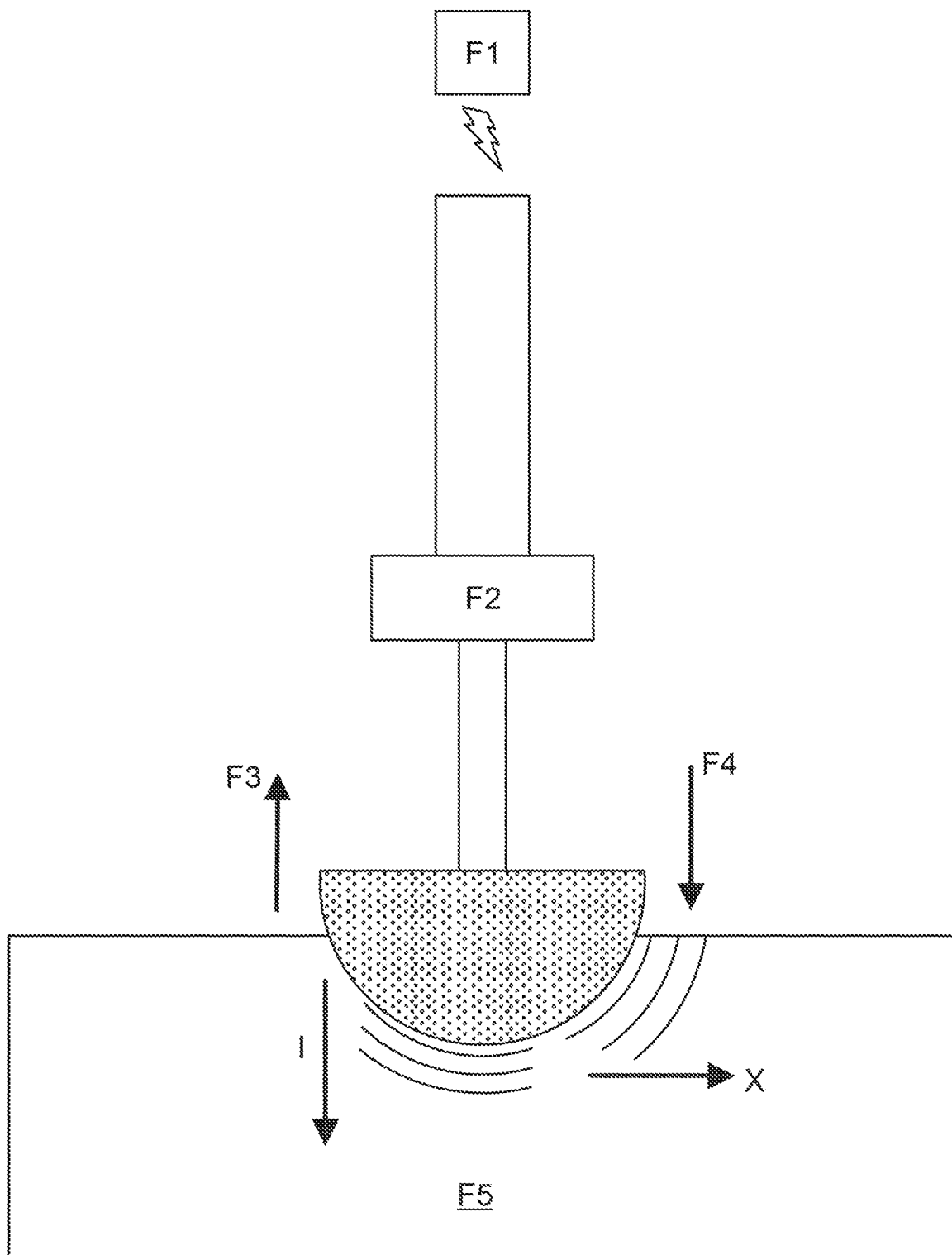
FIG. 2 illustrates an identification of forces in a press fit fixation installation of a prosthesis.

FIG. 2 illustrates an identification of forces in a press fit fixation installation of a prosthesis. These forces, as illustrated, include F1 (applied force), F2 (responsive force in smart tool), F3 (resistive force to installation), F4 (axial extractive force), and/or F5 (force in bone substrate). There may be other forces that may be measured or determined to be correlated, responsive, and/or related to these forces. In some circumstances, multiple related or correlated forces may be "fused" into a fusion force that provides a robust evaluation of the component forces, with any appropriate individual weightings of component forces in the fused force. That is some embodiments, a press-fit fixation may be assessed based upon contributions from multiple forces fused together rather than evaluations of individual forces or derivatives thereof.

When press fitting an acetabular component into an undersized cavity, one may expect to encounter three regions with distinct characteristics: (a) poor seating and poor pull out force; (b) deep insertion and good pull out force; and (c) full insertion which may also have strong fixation but includes higher (and possibly much higher) risk of fracture.

Some embodiments may exhibit relationships between extraction force (F4) and cup insertion CI with respect to similarity and proportionality to a standard stress/strain curve of material deformation.

While two collisions occur during the process of prosthesis impaction into bone in some embodiments for each force application, a proximal collision is usually elastic and typically presents a maximum value of F1 for any given impact energy E of the force application. A distal collision is conversely initially inelastic and progresses to an elastic state as insertion no longer occurs. In some experiments, force measurements in the impaction rod (F2) and bone (F5) may represent the distal collision.

Figure 3:
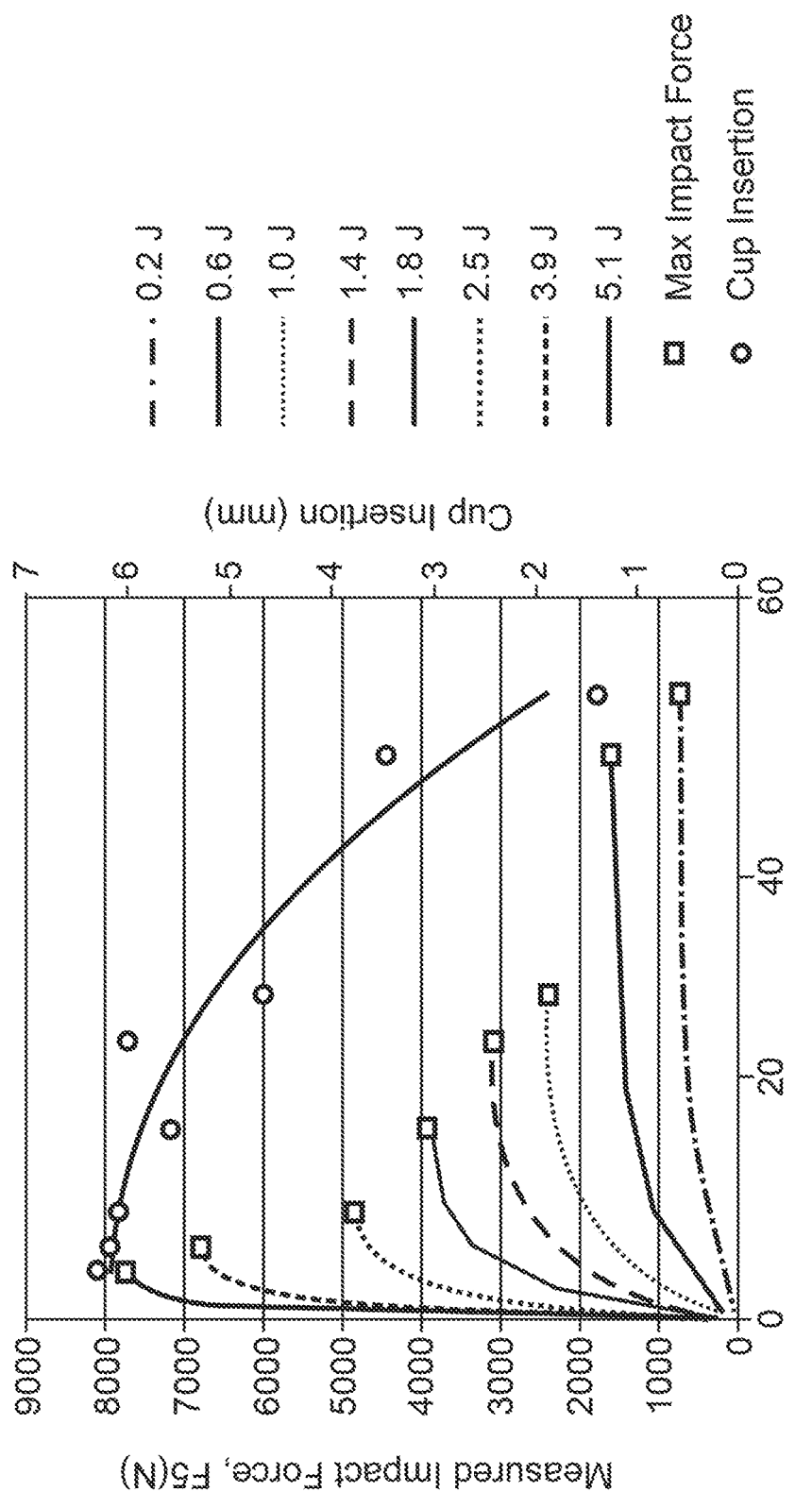
FIG. 3 illustrates a set of relationships between measured impact force (e.g., F5), number of impacts (NOI), cup insertion (CI), and impact energy Joules (J)

FIG. 3 illustrates a set of relationships between measured impact force (e.g., F2, F3, and/or F5 and/or derivatives and/or combinations thereof), number of impacts (NOI), cup insertion (CI), and impact energy Joules (J). Experiments in the study of vibratory insertion of orthopedic implants [Published Patent App. Invasive Sensing Mechanism: Pub No. 20170196506, incorporated herein by reference in its entirety for all purposes] where an oversized acetabular prosthesis, Zimmer Continuum Cup (62 mm) was inserted into an undersized (61 mm) bone substitute cavity (20 lbs Urethane foam), using three different insertion techniques including controlled impaction, vibratory insertion, and constant insertion. The forces at play were considered in FIG. 2. An 8900 N force gauge was placed within the polyurethane sample to measure forces in the cavity F5.

With the controlled impaction technique we tested eight-drop heights producing a range of impact energies from 0.2 J to 5.0 J corresponding to impact forces ranging from 550 N to 8650 N. Five replications were performed for each height, with a total sample population of 40 units. For each sample, impacts were repeated at a selected drop height until implant displacement between impacts were within the measurement error of 0.05 mm. Peak impact force in bone F5, total cup insertion CI, and number of impacts NOI to full insertion were recorded for each sample. Cup stability was measured by axial extraction force by means of a pull test using Mark 10 M5-100 test stand and force gauge. The results are shown in Table I.

TABLE I

Drop Test Results

| Drop Height (mm) | Impact Energy (J) | Maximum Impact Force in bone F5 (N) | Mean Number of Impacts | Cup Insertion (mm) | Extraction Force F4 (N) |
|---|---|---|---|---|---|
| 10 | 0.2 | 774 | 52 | 1.4 | 71 |
| 30 | 0.6 | 1641 | 47 | 3.5 | 258 |
| 50 | 1.0 | 2437 | 27 | 4.7 | 480 |
| 70 | 1.4 | 3104 | 23 | 6.0 | 676 |
| 90 | 1.8 | 3927 | 16 | 5.6 | 765 |
| 130 | 2.5 | 4870 | 9 | 6.1 | 827 |
| 200 | 3.9 | 6814 | 6 | 6.2 | 849 |
| 260 | 5.1 | 7757 | 4 | 6.3 | 867 |

These data indicate that every level of impact energy is associated with a final depth of cup insertion CI, a plateauing of the force response in bone F5 to an asymptote, and a certain rate of insertion inversely related to the number of impacts NOI required for insertion. As an example, it took 4 impacts for a maximum applied force of 7757 N to insert the cup 6.3 mm, whereas it took 52 impacts for a maximum applied force of 774 N to insert the cup 1.4 mm.

Figure 4:
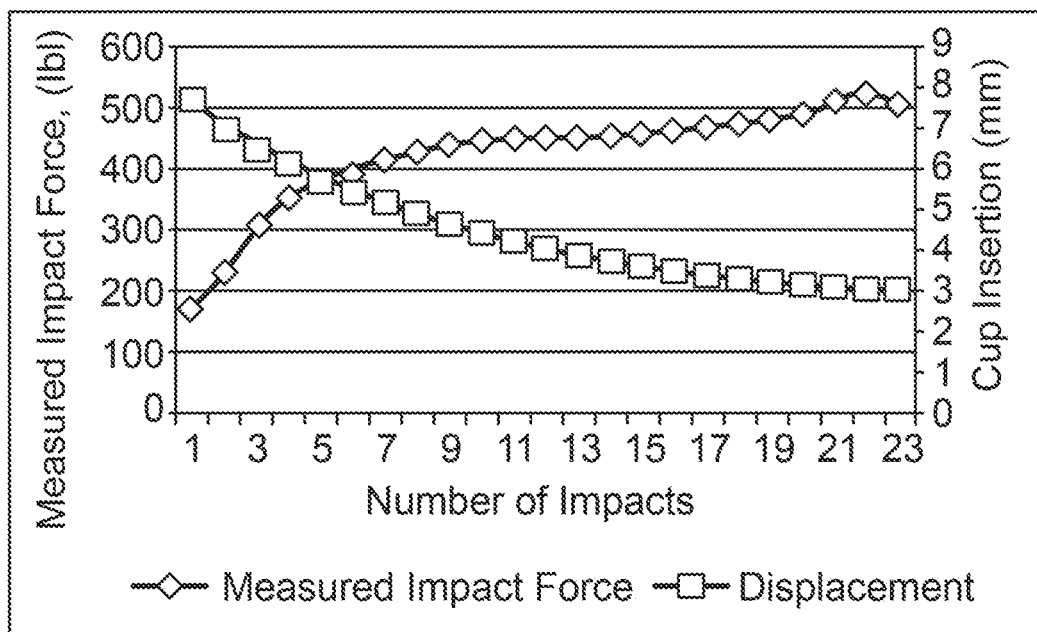
FIG. 4 illustrates a relationship of force in bone (e.g., F5) and cup insertion (CI) for 1.0 Joules (J)
Figure 5:
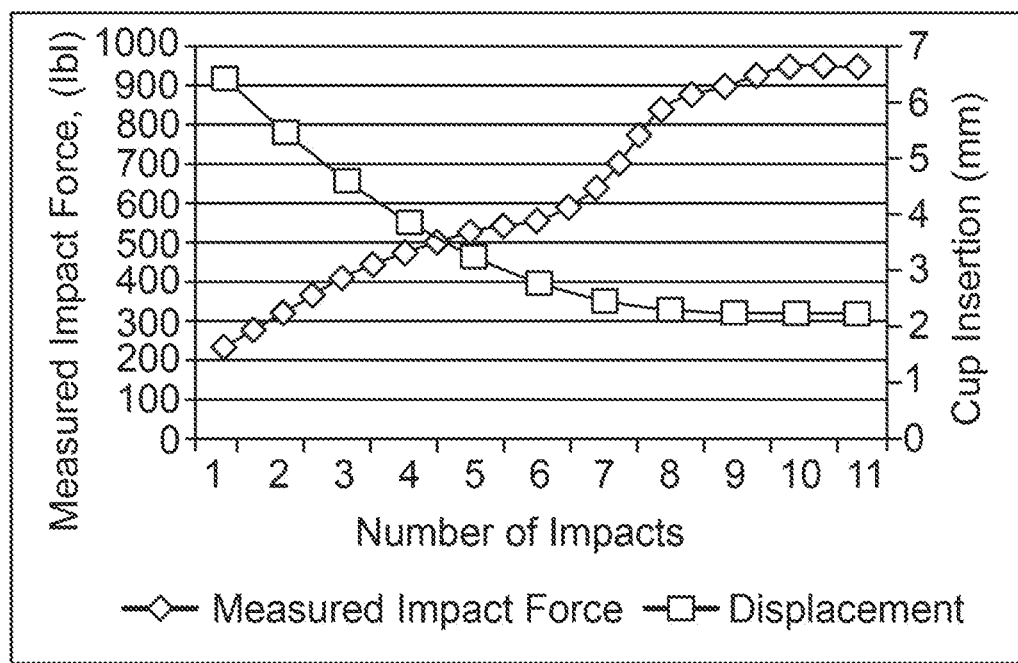
FIG. 5 illustrates a relationship of force in bone (e.g., F5) and cup insertion (CI) for 1.8 Joules (J)

FIG. 4 illustrates a relationship of force in bone (e.g., F5) and cup insertion (CI) for 1.0 Joules (J) and FIG. 5 illustrates a relationship of force in bone (e.g., F5) and cup insertion (CI) for 1.8 Joules (J). A decaying of the force response in bone F5 to an asymptote (when $\Delta F5$ approaches 0) could be used as a parametric value guiding incremental application of energy to obtain optimal press fit fixation of implants. This phenomena is identified herein as the rigidity factor (or rigidity metric) which appears to reach a maximum for any given impact energy.

Figure 6:
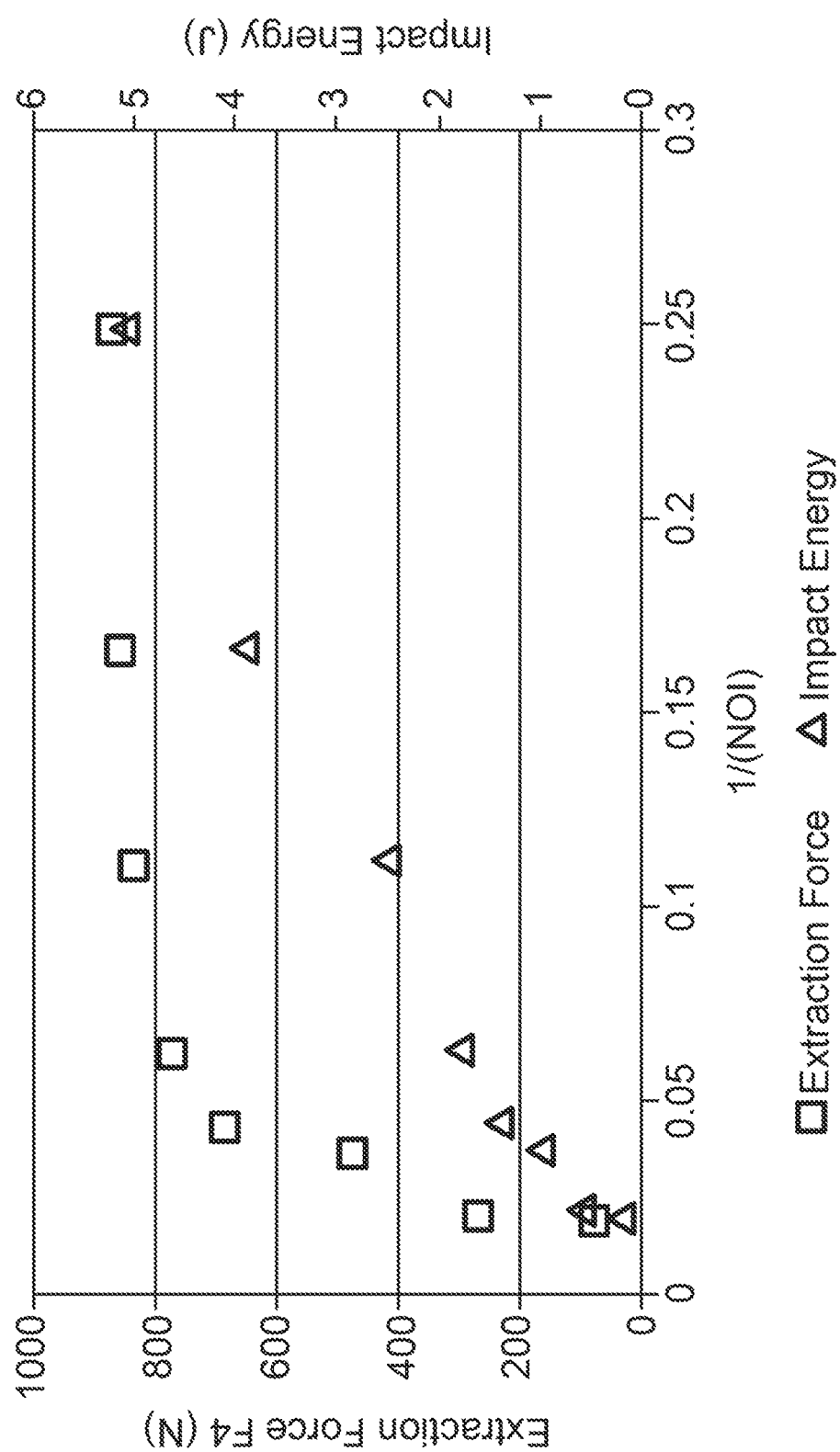
FIG. 6 illustrates a relationship between a rate of insertion (1/NOI), extractive force (e.g., F4), and impact energy.

FIG. 6 illustrates a relationship between a rate of insertion (1/NOI), extractive force (e.g., F4), and impact energy. A direct relationship was observed between rate of insertion, inversely related to number of impacts NOI, and the extractive force F4, and this phenomenon is termed an elasticity factor (or elasticity metric), which appears to provide a real-time estimation of the extractive force of the implant/bone interface, as well as an indirect measure of the elastic/plastic behavior of the aperture of bone. A decaying rate of insertion is considered and appears inversely related to a number of impacts and suggests an ultimate stress point of the cavity aperture.

Figure 7:
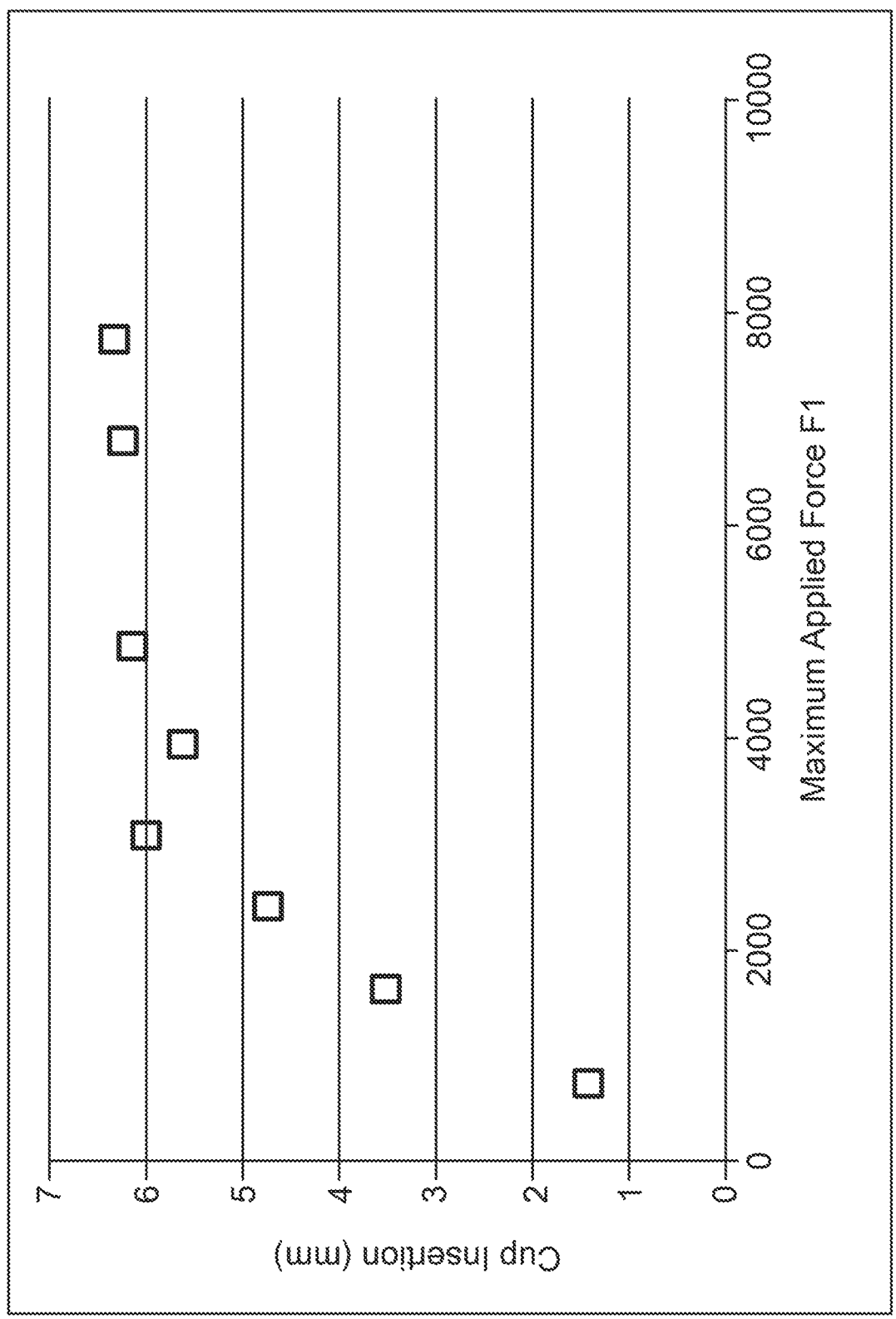
FIG. 7 illustrates a relationship between maximum applied force (e.g., F1) and cup insertion (CI)
Figure 8:
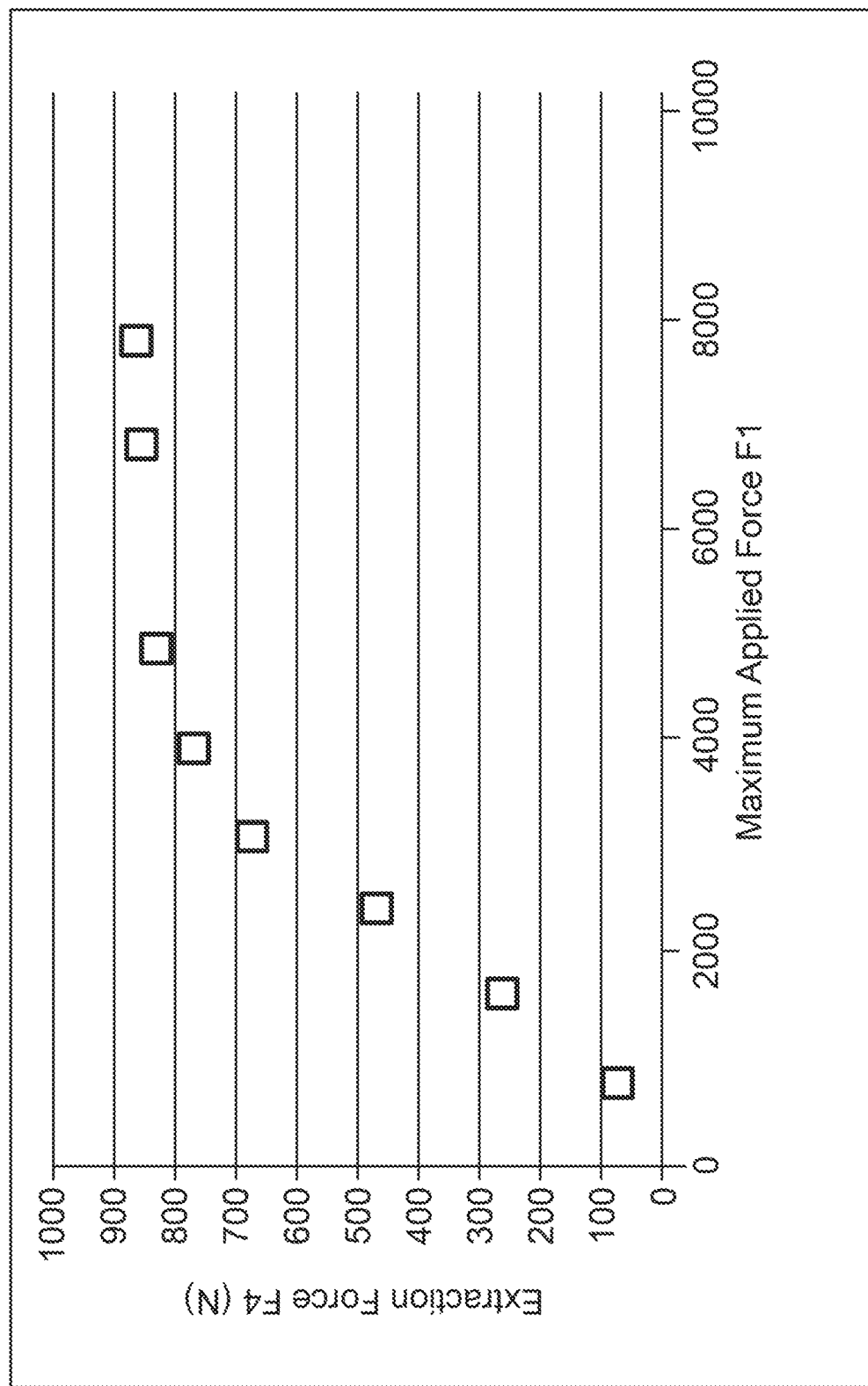
FIG. 8 illustrates a relationship between maximum applied force (e.g., F1) and an extractive force (e.g., F4)

FIG. 7 illustrates a relationship between maximum applied force (e.g., F1) and cup insertion (CI) and FIG. 8 illustrates a relationship between maximum applied force (e.g., F1) and an extractive force (e.g., F4). The relationships of applied force F1 and cup insertion CI as well as applied force F1 and extractive force F4 were evaluated and showed characteristic non-linear curves.

Of note was the observation that an inflection point or (range) exists above which increased applied force F1 (impact energies) did not appear to provide any meaningful increase in cup insertion CI or extraction force F4. As example 1.8 joules of impact energy produced 5.6 mm (89%) of cup insertion CI and 827 N (88%) of extraction force F4. An additional 3.3 joules of impact energy was required for a marginal insertion gain of 0.7 mm and extraction force gain of 102 N.

Questions were posed as to how much force is required for optimal press fit fixation? Does the insistence to fully seat the cup work against the patients and surgeon? Do surgeons risk fracturing the acetabulum in the desire to fully seat the cup? The existence of polar gaps in acetabular press fit fixation have been clinically studied and shown no adverse outcomes.

It was contemplated that a point or (a small range), defined by the parametric values above, exists which could produce the best fixation short of fracture (BFSF) and an embodiment may propose BFSF as an ideal endpoint for all press fit joint replacement surgery. BFSF may, in some situations, act not only as a point of optimal press fit, but also define a sort of speed limit or force limit for the surgeon.

In this application an embodiment may develop a method described as the invasive sensing mechanism (ISM), by which the end point BFSF can be defined in four chosen systems. Additionally, an embodiment may develop an Automatic Intelligent Prosthesis Installation Device (AI-PID) that can quantitatively access this point. The following concept is proposed for a fixation algorithm to achieve BFSF for any implant/cavity interface. (A Double Binary Decision)

Figure 9:
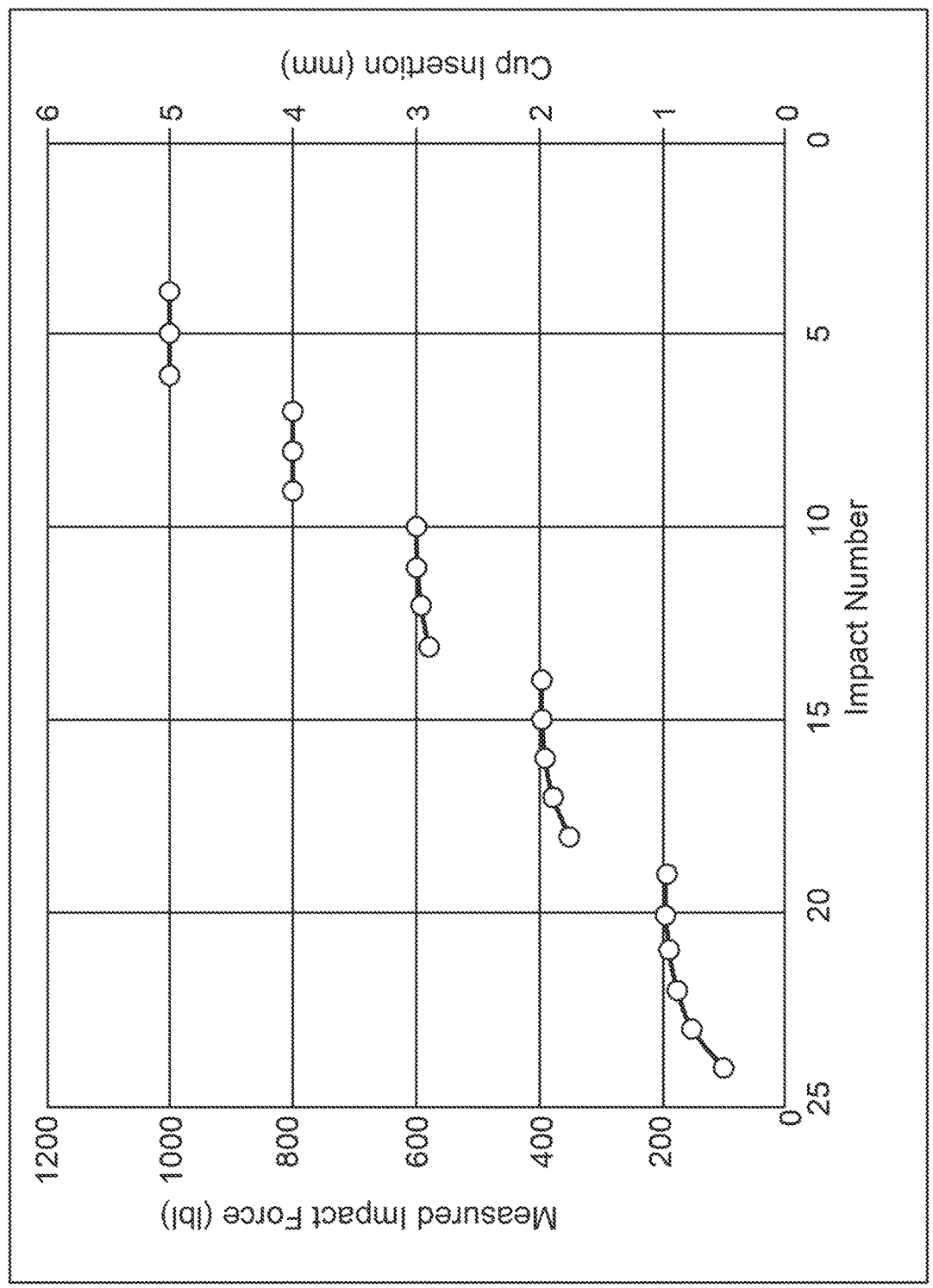
FIG. 9 illustrates a representative force response for incrementing impact energies.

FIG. 9 illustrates a representative force response for incrementing impact energies. The rigidity factor represented by plateauing levels of force in bone (e.g., F5) can be used to guide incremental increase in impact energy J. For any impact energy J, as the force in bone plateaus to a maximum, no further insertion is occurring; a decision can be made as to whether impact energy should be increased or not. This is the first binary decision. The elasticity factor represented by the speed of insertion of an implant (e.g., inversely related to number of impacts (NOI) required for insertion) can be used to guide the surgeon as to whether application of force should continue or not. This is the second binary decision. Two binary decisions for BFSF which may not include full seating.

Figure 10:
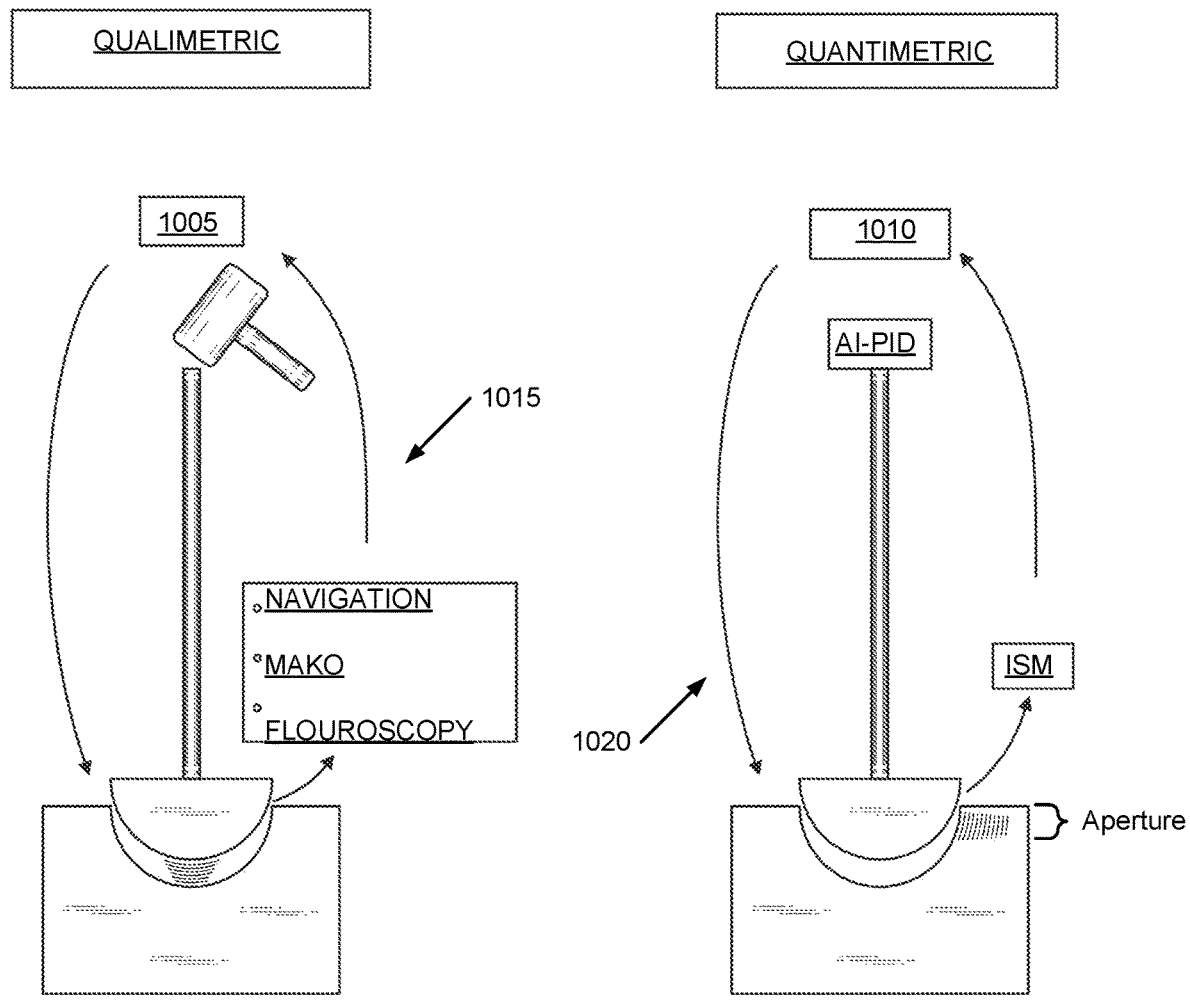
FIG. 10 illustrates a comparison of a quantitative system versus a qualimetric system for evaluating a real time non-visually tracked press fit fixation.

FIG. 10 illustrates a comparison of a quantimetric system (including a measured quantitative determination/use of BFSF) versus a qualimetric system (typically based on a visual qualitative assessment of a depth of insertion) for evaluating a real time non-visually tracked press-fit fixation. An invasive sensing mechanism (ISM) and an automatic intelligent prosthesis installation device (AI-PID) may standardize an application of force and an assessment of a measured quality of fixation in joint replacement surgery, through exploitation of the relationships between the force responses in the installation tool, bone and the interface.

The qualimetric system includes various visual tracking mechanisms (e.g., computer navigation, MAKO assistant, fluoroscopy, and the like) in which an uncontrolled force is applied manually such as by a mallet 1005. The quantitative system operates an insertion agency 1010 which enables application of controlled forces (e.g., force vectors of controlled direction and/or controlled magnitude). The insertion agency may involve ISM which, in some implementations, may assess the stress response of bone at the implant/bone interface as opposed to qualimetric discussed in the above paragraph that does visual tracking.

The qualimetric system includes a striking-evaluation system 1015 in which a mallet strikes a rod which drives a prosthesis into a prepared cavity. The surgeon then qualitatively assesses the placement using secondary cues (audio, tactile, visual imaging) to estimate a quality of insertion and assume a quality of fixation. This cycle of strike and assess continues until the surgeons stop, often wondering whether stopping is appropriate and/or whether they have struck the rod too many times/too hard.

In contrast, a quantitative cycle 1020 in the quantimetric system includes operation of an insertion agency, measurement of force response(s) to determine elastic and rigidity factors, and use these factors to determine whether to continue operation and whether to modify the applied force from the insertion agency. The quantitative system assumes BFSF and optimal press-fit fixation relies primarily on a cavity aperture of a relatively oversized prosthesis/relatively undersized cavity which provides a contact area around a "rim" of the cavity where bone contacts, engages, and fixates the prosthesis. A depth of the aperture region may depend upon a degree of lateral compression of the prepared bone as the prosthesis is installed.

The parametric values of the quantimetric system provide meaningful actionable information to surgeons as to when to increment the magnitude of force, and as to when to stop application of force. Additionally, surgeons currently utilize qualitative means (auditory and tactile senses) as well as auxiliary optical tracking means (fluoroscopy, navigation) to assess the depth of insertion and estimate a quality of fixation during press fit arthroplasty. Application of force to achieve press fit fixation is uncontrolled and based on human proprioceptive and auxiliary optical tracking means. The optimal endpoint for press fit fixation remains undefined and elusive.

An embodiment may include development of a reliable quantitative technique for real-time intra-operative determination of optimal press fit, and the development of a smart tool to obtain this point automatically. The ability to base controlled application of force for installation of prosthesis in joint replacement surgery on the force response of the implant/bone interface is an innovative concept allowing a quantimetric evaluation of the implant/bone interface.

An embodiment for a quantimetric system may include a hand-held tool (See, e.g., FIG. 1) that can produce impact energies of the necessary magnitude and accuracy. A variety of actuation methods can be used to create controlled impacts, including pneumatic actuators, electro magnetics actuators, or spring-loaded masses. An example implementation using pneumatic, vibratory, motorized, controlled, or other actuation The device shall have industry standard interfaces in order to allow for use with a variety of cup models.

A slide hammer pneumatic prototype is created to allow precise and incremental delivery of energy E. It is equipped with inline force sensors in order to measure resulting forces F1 and F2 and controlled by integrated electronics that provides analysis of F1, F2, ΔF2, number of impacts, and impact energy E. Programed algorithms based on the double binary system described herein will produce successive impacts of a known energy, making two simultaneous binary decisions before each impact: (a) modify energy or not; and (b) apply energy or not. These two binary decisions will be based on parametric values produced by the control electronics, which provides an essential feedback of the implant/bone interface, and the elastic response of bone at the aperture. The following algorithm provides a basic example of the double binary decision making process.

A method for assessing a seatedness and quality of press fit fixation includes a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level.

1. Apply energy E1 and measure F2, number of impacts (NOI), ΔF2.
2. Monitor F2 over number of impacts (NOI), and/or monitor ΔF2 as it approaches zero.
3. When ΔF2 approaches zero, insertion is not occurring for that particular energy E1. If NOI required to achieve this point is sufficiently large (low speed of insertion) as determined by the control algorithm, then E1 is increased to E2
4. Continue steps 1 through 3 until the NOI required for ΔF2 to approach zero is sufficiently small (high speed of insertion) as determined by the control algorithm.
5. The smart tool may be implemented so it will not generate automated impacts after this level is reached. Additional increase in energy E is not recommended but can be produced manually or after a considered override by the surgeon. For example, it may be that no more than one incremental manual increase is recommended or established as a best practice.

Validation of the tool may be performed by comparing the quality of insertion (extractive force F4) produced by AI-PID with those produced by a mallet and standard impaction techniques. Specifically, the two distinct endpoints of (i) BFSF (achieved through AI-PID) and (ii) full seating (achieved through mallet strikes) will be compared to determine differences in the extractive force F4 and fracture incidence. A risk benefit analysis will be done to determine whether additional impacts and insertion beyond BFSF provided any significant value as to implant stability, or conversely led to increased incidence of fracture of the cavity. (As noted herein, it may be the case that BFSF may be achieved without full seating, a stated goal of many conventional procedures.)

It is anticipated that the measurements of F2, and ΔF2 and its comparative analysis with respect to number of impacts NOI will provide a principled and organized process for application of energy to achieve a desired endpoint of fixation BFSF. We expect that the first order relationship of ΔF2 will provide the information as to whether, for any particular level of applied energy, insertion is occurring or not; providing a guidance as to whether applied energy should be increased. We expect the rate of ΔF2 decay to zero will provide information about elastic/plastic behavior of the aperture, indicating when the maximum strain X, normal force FN, and extractive force F4 at the aperture of the bone cavity have been achieved. We anticipate reproducing the results of phase I aim 1, namely that there is a strong correlation between pull force F4 and rate of decay of ΔF2, that an inflection point exists in the elasticity factor, beyond which addition of impact energy will lead to marginal gains in extraction force F4 and depth of insertion, mitigating against goal of full seating as the best policy.

We have indicated that the grasp of bone (bone substitute) on an implant at the aperture can be modeled in some cases by formula such as FN*Us where FN represents the normal forces at the interface, and Us represents the coefficient of static friction. FN is estimated by Hooke's Law and is represented by K.X, where K represents the material properties of bone including the elastic and compressive moduli and X represents the difference in diameter between the implant and the cavity. We note that the value of K can vary dramatically between different ages and sexes. We anticipate this tool to be capable of automatically producing the proper amount of impact energy E, cup insertion CI, stretch on bone X, normal force FN, and extractive force F4 to achieve optimal press fit for patients of various ages and sexes, eliminating an over reliance on surgeon senses and experience.

Having access to this interface sensing phenomena, an embodiment may develop a simple controlled impaction process that allows the surgeon to quantize the impact energy, and deliver it in a controlled and modulatable fashion based on the above two parametric value representing the stress/strain behavior of bone. Some embodiments may develop the concept of controlled force application based on an evaluation of the interface force phenomena (forces felt at the prosthesis/cavity interface). This is in stark contradistinction of uncontrolled application of force with a mallet based on a VISUAL assessment/tracking of the depth of prosthesis insertion (MAKO, all navigation techniques, Fluoroscopy, Nikou—a navigation technique).

There may be many different ways to asses rigidity factor and to asses an elasticity factor. FIG. 11-FIG. 14 illustrates F2 approaching F1 and F5 approaching F1, as well as (ΔF2 approaching 0) and (ΔF5 approaching 0). Additional non-illustrated ways include F3 approaching F1 and ΔF3 approaching 0). As noted herein, data fusion may produce a fusion variable that can measure, evaluate, or indicate rigidity and/or elasticity. For example, one or more of F2, F3, and F5, appropriately weighted, may be fused into a variable that may be used such as by comparing to F1 or delta fused variable compared to a threshold value (such as zero).

Figure 11:
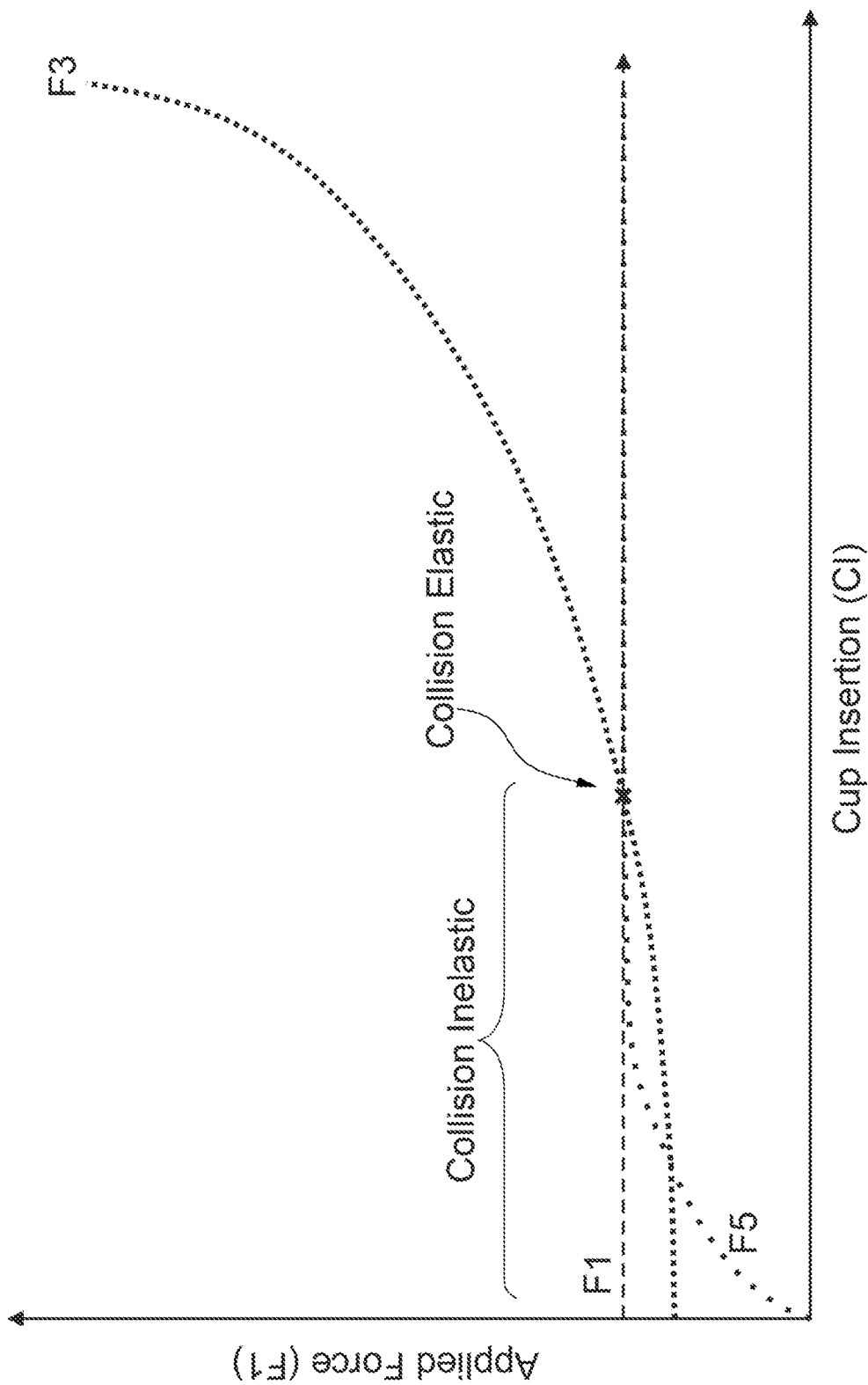
FIG. 11-FIG. 14 illustrate a set of rigidity metric measurements.
Figure 12:
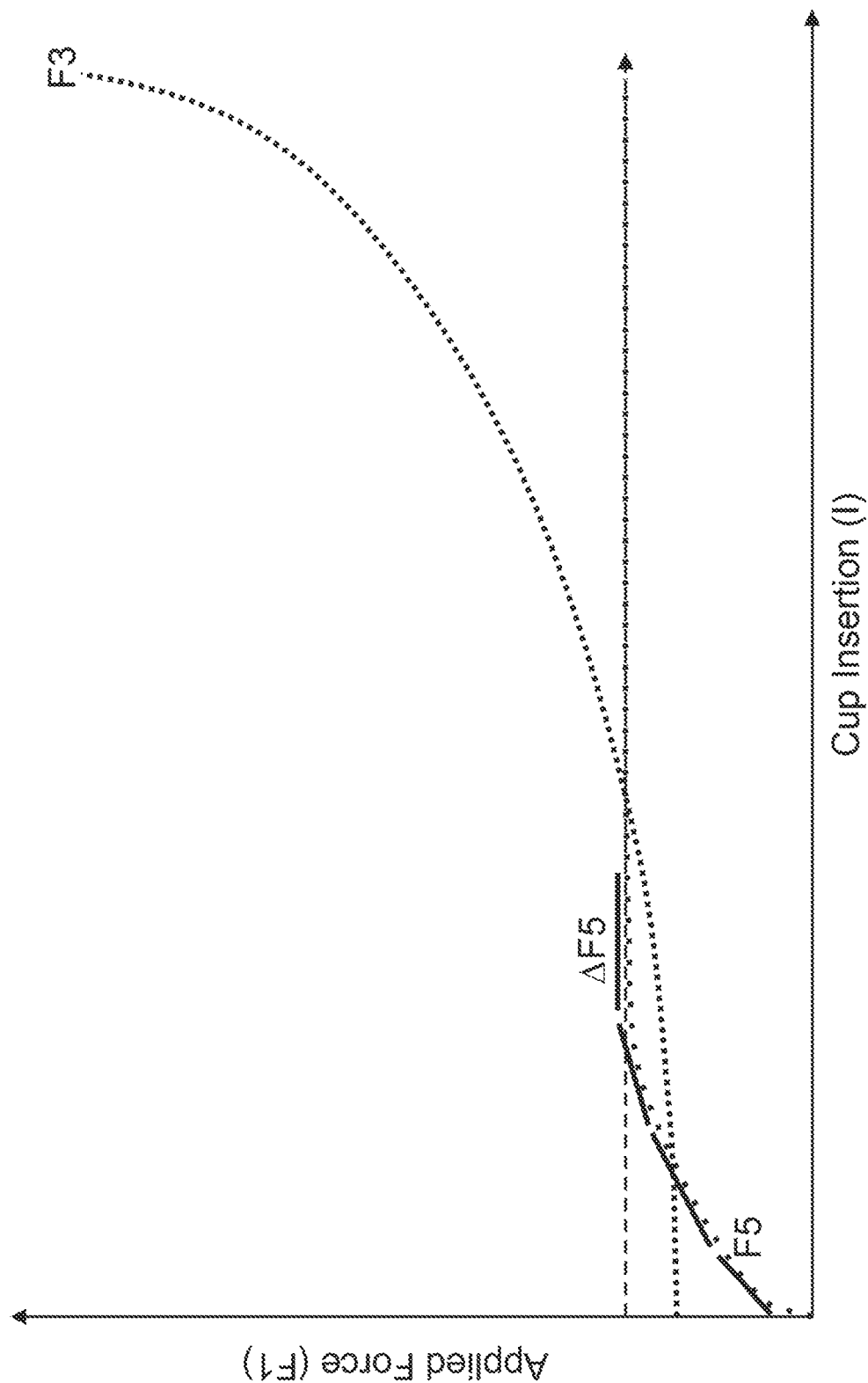
Figure 13:
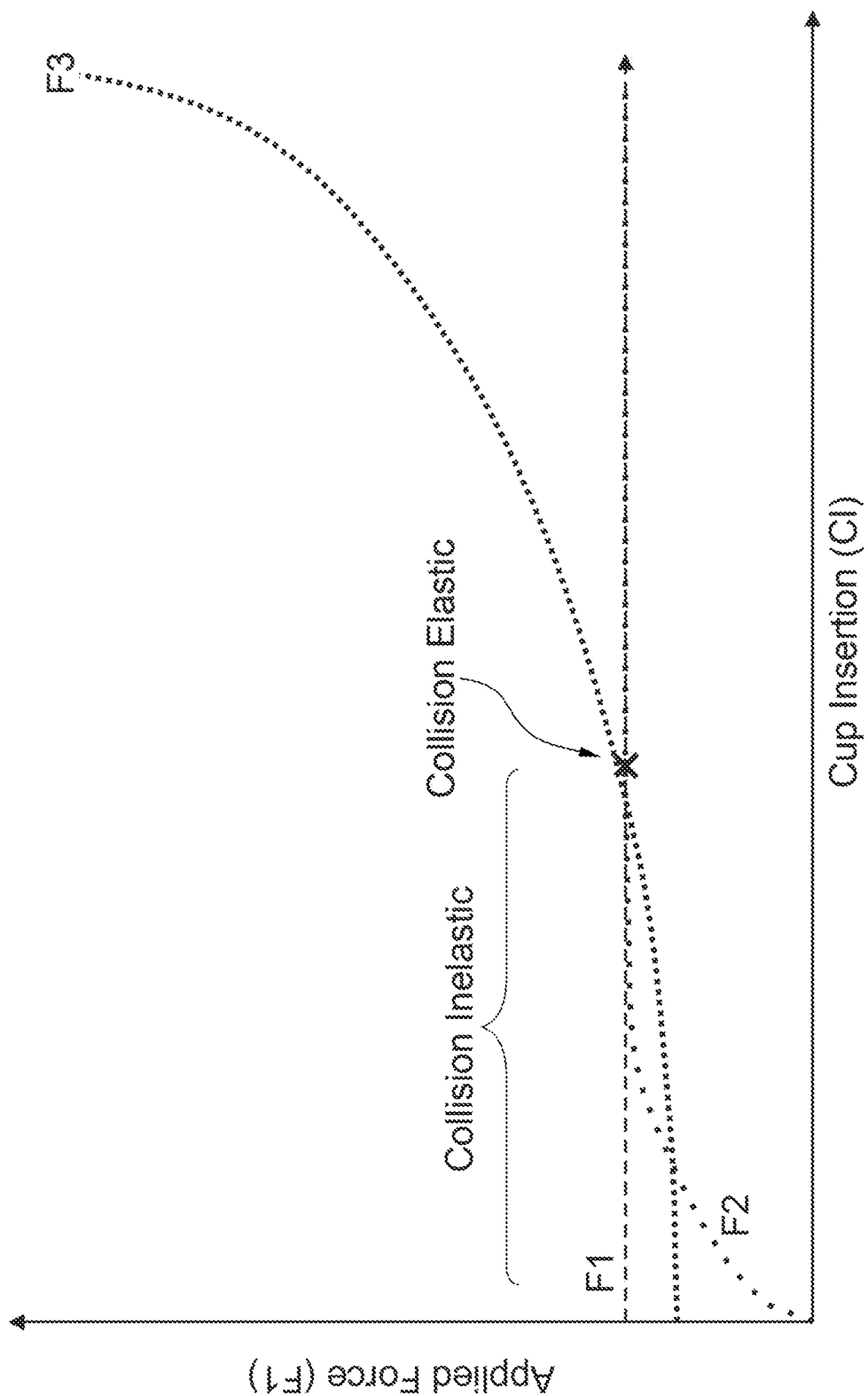
Figure 14:
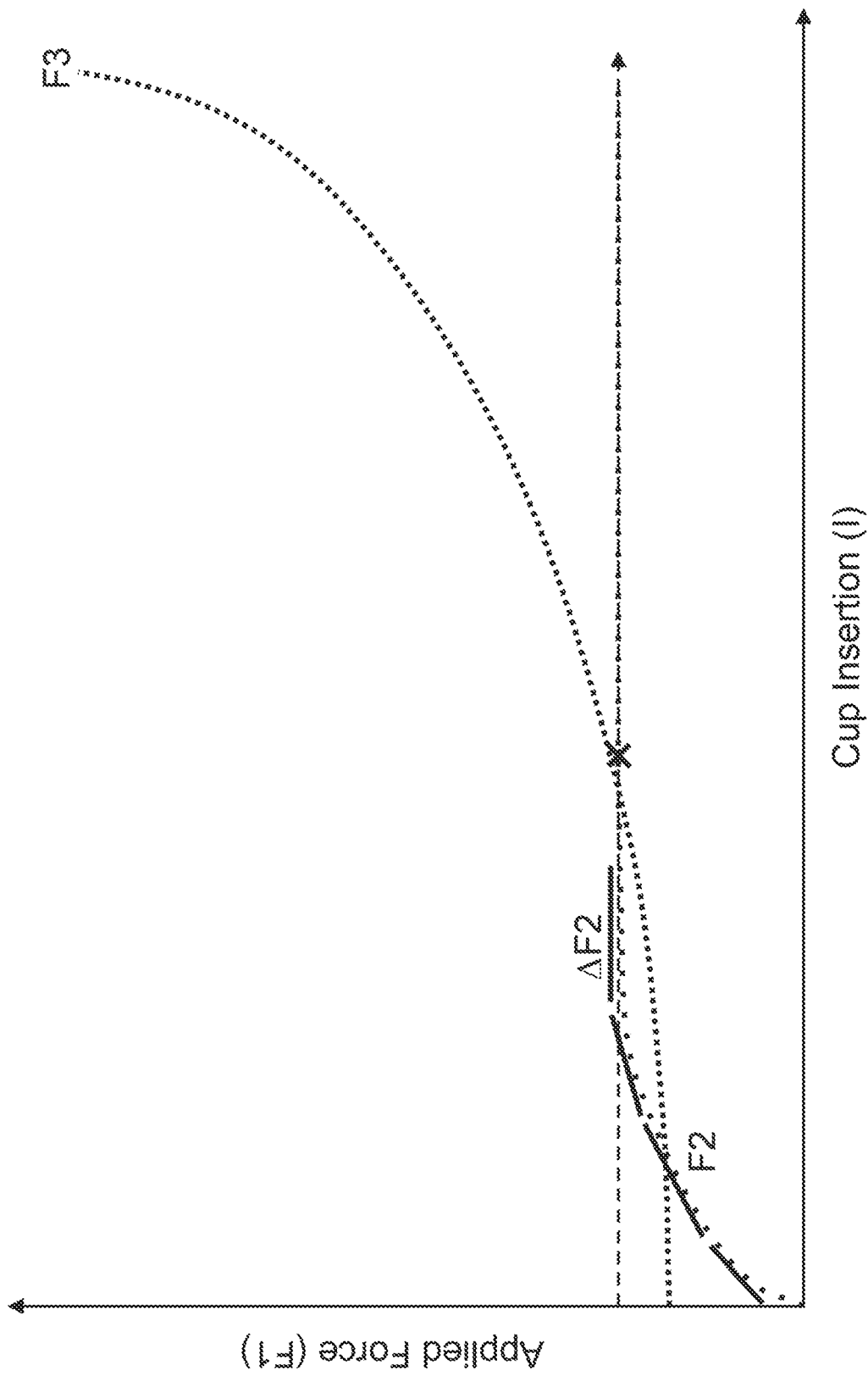

FIG. 11-FIG. 14 illustrate a set of rigidity metric measurements that may be used in the methods and systems described herein. FIG. 11 illustrates a comparison of F5 to F1; FIG. 12 illustrates a comparison of ΔF5 to a predetermined threshold (e.g., 0.0); FIG. 13 illustrates a comparison of F2 to F1; and FIG. 14 illustrates a comparison of ΔF2 to a predetermined threshold (e.g., 0.0).

Figure 15:
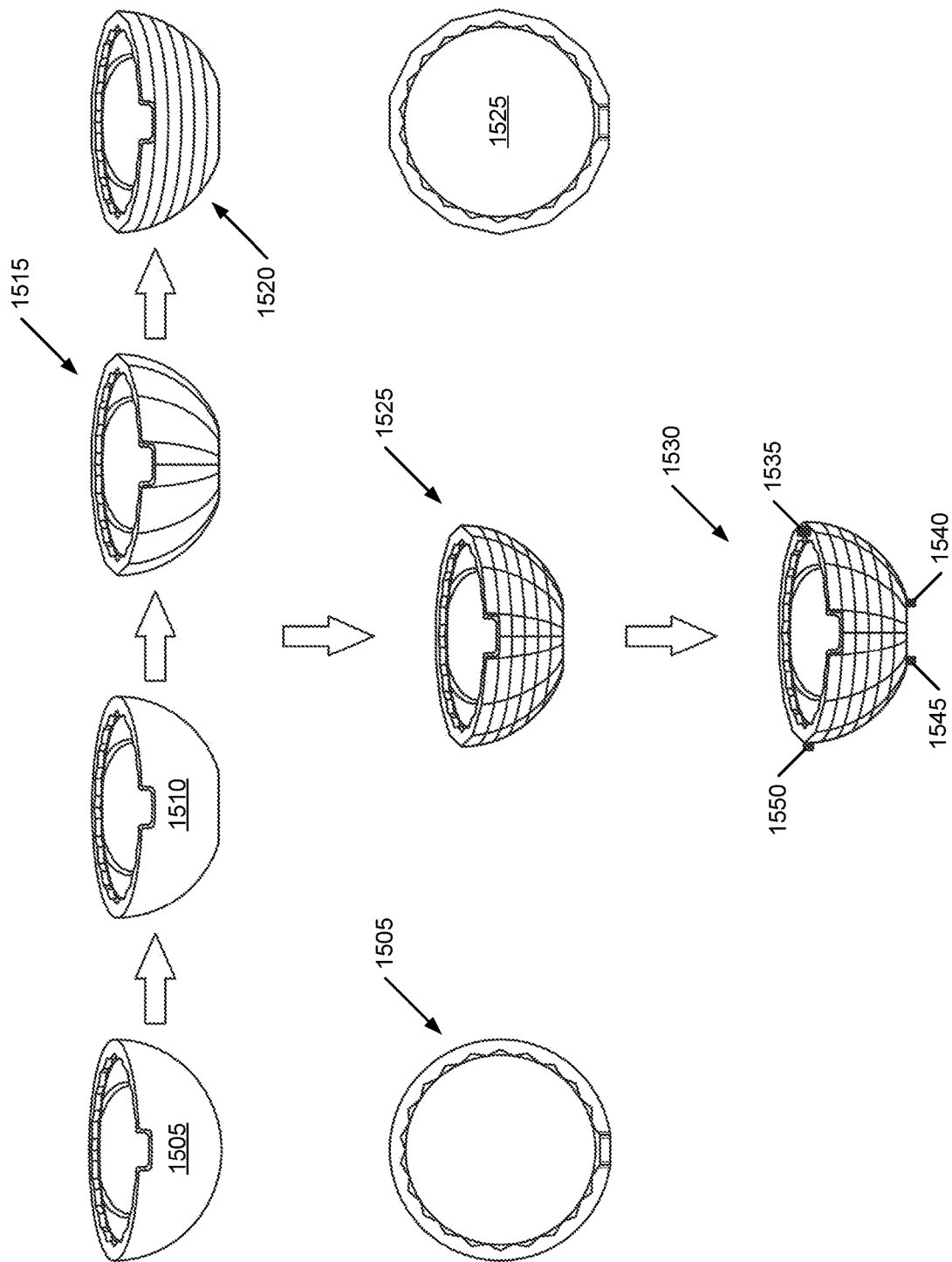
FIG. 15 illustrates an evolution of an acetabular cup consistent with improving press fit fixation.

FIG. 15 illustrates a possible evolution of an acetabular cup 1505 consistent with improving press fit fixation. As noted, a conventional acetabular cup for an implant includes a hemispherical outer surface designed to be installed/impacted into a prepared bone cavity (also hemispherical produced from a generally hemispherical reamer for example).

Different stages of evolution illustrate possible improvements to prosthesis embodiments that are responsive to assumptions and embodiments of the present invention. An assumption of some conventional systems is that full depth of insertion results in a maximum extractive press fit fixation. In contradiction to this assumption, it may be the case that embodiments of the present invention achieve maximum/optimal press fit fixation (BFSF) short of full insertion (i.e., intentional presence of a polar gap).

There may be advantages to reducing polar gaps, and rather than full insertion, a modification to the prosthesis may include a truncated hemisphere (snub nosed) cup 1510. There is a desire to reduce insertion forces while maximizing press fit fixation. Evolution of the prosthesis may incorporate several different ideas, including asymmetric deformation control using a truncated cup with longitudinally extending ribs 1515 and laterally extending planks 1520—the combination of ribs and planks cup 1525 may produce an asymmetric deformation to improve installation (such as making it easier to install and more difficult to remove). Further, a perimeter of an improved cup may include a discrete polygon having many sides. The reduced surface area contacting the prepared cavity may reduce force needed to install while the vertices of the polygon may provide sufficient press-fit fixation. Cup 1525 may include tuned values of the snub, different stiffnesses of ribs and planks, a perimeter configuration of the regular/irregular non-hemispherical polygonal outer surface. These vertices themselves may be angular and/or rounded, based upon design goals of a particular implementation of an embodiment to achieve the desired trade-offs of installation efficiency and press-fit fixation to improve the possibility of achieving BFSF.

These concepts have implications on how the acetabular (all press fit prosthesis) prosthesis are made. If it holds true that the dome of the cup mostly acts like a wedge to cause fracture, it may be best to eliminate the dome (flatten the cup) and change the geometry of the cup to be more like a frustum polygon with nth number of sides, or a hemisphere with a blunted dome.

A. With the ability to provide a proportional amount of force for any particular (implant/bone) interface, we can expect to use just the right amount of force for installation of the prosthesis (not too much and not too little). Additionally we have previously in U.S. patent application Ser. No. 15/234,927, expressly incorporated herein, discussed methods to manufacture prosthesis with an inherent tendency for insertion, MECHANICAL ASSEMBELY INCLUDING EXTERIOR SURFACE PREPAREATION. Specifically, we have descried the concept of two dimensional stiffness incorporated within the body of the prosthesis, which would produce a bias for insertion due to the concept of undulatory motion, typically observed in Eel and fish skin.

FIG. 15 includes a side view of a prosthesis including a two-dimensional asymmetrical stiffness configuration, and illustrates a top view of prosthesis. The prosthesis may include a set of ribs and one or more planks disposed as part of a prosthetic body, represented as an alternative acetabular cup. The body may be implemented in conventional fashion or may include an arrangement consistent with prosthesis P. The ribs and plank(s) are configured to provide an asymmetric two-dimensional (2D) stiffness to body that may be more conducive to transmission of force and energy through the longitudinal axis of the cup as opposed to circumferentially. Ribs are longitudinally extending inserts within body (and/or applied to one or more exterior surfaces of body). Plank(s) is/are laterally extending circumferential band(s) within body (and/or applied to one or more exterior surfaces of body). For example, planks may be "stiffer" than ribs (or vice-versa) to produce a desired asymmetric functional assembly that may provide for an undulatory body motion as it is installed into position.

Based on our understanding of the acetabular prosthesis/bone interface in our Invasive sensing studies in one or more incorporated patent applications and in conjunction with the incorporated '927 application of MECHANICAL ASSEMBELY INCLUDING EXTERIOR SURFACE PREPAREATION, we anticipate that the prosthesis of the future may have different characteristics.

A. The acetabular component may be shaped more like a frustum with Nth (e.g., 160 sides) and an amputated dome. The snubbed dome of the new prosthesis would not engage the acetabular fossa (Cotyloid fossa) allowing the new prosthesis fully engage the stronger acetabular walls/rim (constituted by the ilum, ischium and pubic bones). This shape of prosthesis avoids the possibility of a wedge type fracture which can be produced by the dome of a hemispherical implant.

B. Each angle of the frustum may produce longitudinal internal rib extending from the rim distally, (developed within the structure of the prosthesis by additive manufacturing by controlling the material properties of crystalline metal), that is more flexible than the horizontal stiffer planks that extend from the rim to the snub distally in a circumferential fashion. (See the incorporated '927 application). This shape of prosthesis will have a strong bias for insertion due to undulatory motion, and will require less force for installation.

Permanent or Removable Sensors on the surface of the Prosthesis.

A. As described herein, in some experiments that when F2 approaches F1, that in fact F1=F2=F3=F5. That is, when the implant/bone collision becomes elastic, the resistive force at the interface F3 and the forces felt in bone F5 can be inferred from applied force F1 and force felt in tool F2. This can provide the surgeon valuable information about the forces she is imparting to the bone. We also contemplate that F3 and F5 can be directly measured by application of mechanical and biologic sensors directly on a sensing prosthesis 1530. We believe given the mass production and ubiquitously available sensors, at some point, the prosthesis of the future would be equipped with its own sensor (biologic and or mechanical) to convey to the surgeon the forces being imparted into the bone, to prevent excessive forces on bone, as well as to prevent loose fitting prosthesis. Sensors on the applied on the surface of the prosthesis to measure interface or dome pressure (F3 or F5) can be permanent or removable i.e., a slot on the side of the prosthesis can allow incorporation of a small sliding sensor to provide information about the interface to the system. Examples of incorporated sensors, one or more which may be used, may include an internal sensor 1535, a mechanical sensor 1540, a biologic sensor 1545, and an external sensor 1550.

B. Data Fusion of F2, F5, F3 for most sensitive evaluation of stress response of Bone at the Implant Bone Interface—multiple parameters are weighted and merged or fused that may provide a robust parameter offering improved performance over reliance on a single parameter.

2. Application of Force based on a Sensory (Not Visual) Evaluation of Implant/Bone Interface.

A. For years surgeons have applied uncontrolled force to impact prosthesis into bone, and have assessed the quality of insertion by human visual, tactile and auditory means. More recently surgeons have begun to use visual tracking means such as fluoroscopy, computer navigation (including Nikou), and MAKO techniques to assess depth of insertion. We are the first to suggest that the application of force for installation of prosthesis should be predicated on the force sensing activity of the prosthesis/bone interface. This is a new technique that predicates application of force for installation of prosthesis to be based (NOT VISUAL TRACKING MEANS—depth of insertion) but rather (FORCE SENSING MEANS OF THE INTERFACE—proof resilience). This is a novel concept that will eliminate too tight and too loose press fit fixation of all prosthesis, and associated problems such as subsidence, loosening, and infection.

Figure 16:
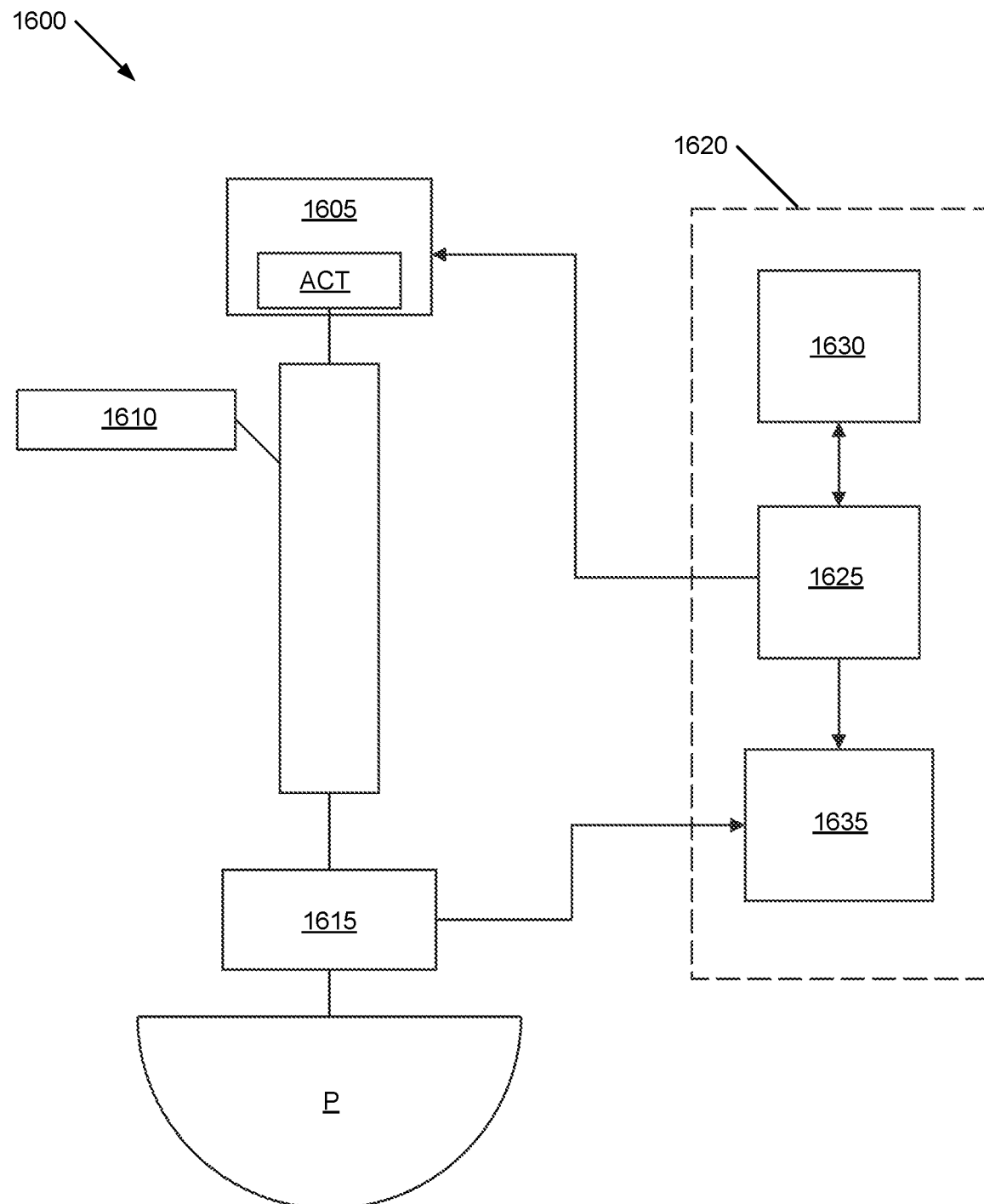
FIG. 16 illustrates a particular embodiment of a $BMD_X$ force sensing tool.

FIG. 16 illustrates a particular embodiment of a $BMD_X$ force sensing tool 1600. Tool 1600 allows indirect measurement of a rate of insertion of an acetabular cup and may be used to control the impact force being delivered to a prosthesis based upon control signals and the use of features described herein. Tool 1600 may include a controllable force applicator (e.g., an actuator) 1605, an impaction transfer structure 1610 (e.g., impaction rod), and a force sensor 1615.

Applicator 1605 may include a force sensor to measure/determine F1 (in some cases applicator 1605 may be designed/implemented to apply a predetermined and known a priori force.

Structure 1610 transfers force as an insertion agency (for prosthesis implant applications) to prosthesis P and sensing system 1615 measures a realtime (or near realtime) force response of prosthesis P to the insertion agency while it is being implanted into the implant site. There are many different possible force response mechanisms as described herein. For example, F2, F3, F5, and first/second order derivatives and combinations thereof as noted herein. In some cases, sensing system 1615 may include in-line or external sensor(s) associated with or coupled to structure 1610. In other cases, some embodiments of system 1615 may include sensor(s) associated with the bone or cavity or other aspect of the cavity, prosthesis, cavity/prosthesis interface or other force response parameter. System 1615, as noted herein, may include multiple concurrent sensors from different area including one or more of tool, prosthesis and bone/cavity.

One representative method for force measurement/response would employ such a tool 1600. Similar to the impaction rod currently used by surgeons, tool 1600 may couple to an acetabular cup (prosthesis P) using an appropriate thread at the distal end of structure 1610. Applicator 1605 may couple to a proximal end of structure 1610, and create an insertion agency (e.g., controlled and reproducible impacts) that would be applied to structure 1610 and connected cup P. A magnitude of the impact(s) would be controlled by the surgeon through a system control 1620, for example using an interface such as a dial or other input mechanism on the device, or directly by the instrument's software. System control 1620 may include a microcontroller 1625 in two-way communication with a user interface 1630 and receiving inputs from a signal conditioner 1635 receiving data from force sensing system 1615. Controller 1625 is coupled to actuator 1605 to set a desired impact profile including a set of force applications that may change over time as described herein.

Sensing system 1615 may be mounted between structure 1610 and acetabular cup P. System 1615 may be of a high enough sampling rate to capture the peak force generated during an actuator impact. It is known that for multiple impacts of a given energy, the resulting forces increase as the incremental cup insertion distance decreases/

This change in force given the same impact energy may be a result of the frictional forces between cup P and surrounding bone of the installation site. An initial impact may have a slow deceleration of the cup due to its relatively large displacement, resulting in a low force measurement. The displacement may decrease for subsequent impacts due to the increasing frictional forces between the cup and bone, which results in faster deceleration of the cup (the cup is decelerating from the same initial velocity over a shorter distance). This may result in an increase in force measurement for each impact. A maximum force for a given impact energy may be when the cup P can no longer overcome, responsive to a given impact force from the actuating system, the resistive (e.g., static friction) forces from the surrounding bone. This results in a "plateau", where any subsequent impact will not change either the insertion of cup P or the force measured.

In some embodiments, this relationship may be used to "walk up" the insertion force plot, allowing tool 1600 to find the "plateau" of larger and larger impact energies. By increasing the energy, the relationship between measured impact force and cup insertion should hold until the system reaches a non-linear insertion force regime. When the non-linear regime is reached, a small linear increase in impact energy will not overcome the higher static forces needed to continue to insert the cup. This will result in an almost immediate steady state for the measured impact force (mIF of a force application X is about the same as MIF of a force application X+1).

A procedure for automated impact control/force measurement may include: a) Begin operation of an insertion agency with a static, low energy; b) Record the measured force response (MIF); c) continue operation of the insertion agency until the difference in measured impact force approaches zero (dMIF=>0), inferring that the cup is no longer displacing; d) increase the energy of the operation of the insertion agency by a known, relatively small amount; and e) repeat operation of the modified insertion agency until plateau and increasing energy in a fashion (e.g., a linear manner) until a particular plateau patterning is detected. Instead, an increase in energy results in a "step function" in recorded forces, with an immediate steady-state. The user could be notified of each increase in energy, allowing a decision by the surgeon to increase the resulting impact force.

A goal of a validated ISM concept is to produce a sophisticated tool for a surgeon that provides automatic, intelligent prosthesis installation, with the capacity to provide access to an optimal best fixation short of fracture (BFSF) endpoint inherent in any implant/cavity system. This tool will allow surgeons of all walks of life, regardless of level of experience, to obtain the best possible press fit fixation of any cup/cavity system, without fear of too loose or tight press fit, as well as obviating the need for screw fixation with all its attendant problems.

The tool may include a handheld pneumatic instrument with a sliding mass component. It may have the following features: 1) ability to deliver precisely controlled axial impacts of known impact energy E, 2) ability to increase or modify applied force (F1) over the course of use, 3) ability to acquire the resulting F1, F2, F3, and F5 for each impact, 4) ability to automatically control the application of impact energy to optimally seat an acetabular cup (implant) using the algorithms determined in Phase I, 5) communicate data pertaining to ISM and BFSF to the surgeon, 6) allow for manual override and selection of impact energy by the surgeon.

Actuators of applicator 1605 may include a one or more of a wide variety of devices (or combinations thereof), including pneumatic actuators, electro-magnetic actuators, spring-loaded masses, and the like.

The device may have industry standard interfaces in order to allow for use with a variety of cup models. An example implementation using pneumatic actuation is shown in FIG. 11. For the example implementation, the impact energy is controlled through a piston actuation control mechanism and by additional adjustments of sliding mass and travel distance. Once a final actuation method is selected, a working prototype will be designed and fabricated to allow for controlled insertion of acetabulum cups.

The instrument may be equipped with inline force sensors and wireless connectivity in order to determine resulting forces F1, F2, F3, F5 within the system. Applied force F1 and felt force within the tool (F2) will be measured using internal sensors, whereas the forces felt in bone (F5) and at the implant/bone interface (F3) will be measured separately with appropriately placed sensors in the system and the data conveyed to the central processing unit (CPU) through wireless (intranet) systems.

The tool will be controlled by integrated electronics that provide analysis of the inter-relationships between F1, F2, F3, F5 with respect to number of impacts (NOI) to full insertion, and impact energy. The magnitude of the impacts will be controlled by a CPU (FIG. 12) and associated software, where the system control may include a microcontroller in two-way communication with a user interface and receive inputs from a signal conditioner, which receives data (directly or indirectly) from the sensors within the system. The microcontroller will be coupled to the actuator to set a desired impact energy and run a fixation algorithm to obtain endpoint BFSF.

Programmed algorithms based on the binary decision system described in Phase I Specific Aim #1 will produce successive impacts of known energy, making two simultaneous decisions before each impact: 1. Continue applying force or not, and if so, then 2. Increase energy or not. These binary decisions will be based on parametric values produced by the control electronics, which provide essential feedback of the implant/bone interface, and the elastic response of bone at the aperture. The following algorithm provides a basic example of the binary "fixation algorithm" to be incorporated in the control mechanism: (i) apply energy E1 and measure F2, NOI, ΔF2; (ii) monitor F2 over NOI, and/or monitor ΔF2 as it approaches 0; (iii) when ΔF2 approaches 0, insertion is not occurring for that particular energy E1. If NOI required to achieve this point is sufficiently large (low rate of insertion), as determined by the control algorithm, then E1 is increased to E2; (iv) continue steps (i) through (iii) until the NOI required for ΔF2 to approach 0 is sufficiently small (high rate of insertion), as determined by the control algorithm; (v) the sophisticated tool will not generate automated impacts after this level is reached. Additional increase in energy E is not recommended but can be produced manually at the surgeon's discretion. No more than one incremental manual increase is recommended.

As noted earlier, our preliminary data indicate that force measurements directly at the interface (F3), and in bone (F5) will show similar trends and characteristics as F2, such that although independent, they may be considered redundant, complimentary and/or cooperative. We expect to be able to incorporate these data into an independent system architecture and utilize existing data fusion algorithms to potentially produce a higher resolution evaluation of the stress (force) field around the implant/bone interface than with each individual sensor alone.

Validation of the tool will be performed at Excelen and at the University of Minnesota Department of Engineering by comparing the quality of insertion (extractive force F4) produced by AI-PID—which automatically achieves endpoint BFSF—with the quality produced by a mallet and standard impaction techniques accomplished by a board certified orthopedic surgeon blinded to the study. Specifically, the two distinct endpoints of 1. BFSF (achieved through AI-PID) and 2. Full Seating (achieved through mallet strikes) will be compared to determine differences in F4 and fracture incidence. All parameters associated with these two endpoints will be compared and evaluated. Specifically, a risk benefit analysis will be performed to determine whether higher impact energies were required to obtain full seating, and if so, whether the additional impacts provided any significant value as to CI or F4, and whether there was any increase in fracture incidence (failure of the cavity) with either technique.

Interpretation of Results:

Measurements of F2 and ΔF2 and their first and second order derivatives and comparative analysis with respect to NOI to insertion may provide a principled and organized process for application of energy to achieve the desired optimal endpoint BFSF. It is anticipated that the second order relationship of ΔF2 to NOI, alternatively stated as the rate of decay of ΔF2 (how fast ΔF2 approaches 0) may provide an evaluation of elastic/plastic deformation and also contribute to achieving BFSF.

The apparatus, system, and methods described herein relating to invasive sensing measurement in which realtime quantimetrics of an implant at a cavity/implant interface are used to determine or estimate a quantitative assessment of a pressfit fixation of the implant into the cavity may be applied during bone preparation using a bone preparation implement. In the description and discussion herein relating to ISM regarding prosthesis P (e.g., an implant such as an acetabular cup), the tool may instead or additionally support a bone preparation implement P (P is understood to refer to an implant or a bone preparation implement for purposes of this application).

Figure 17:
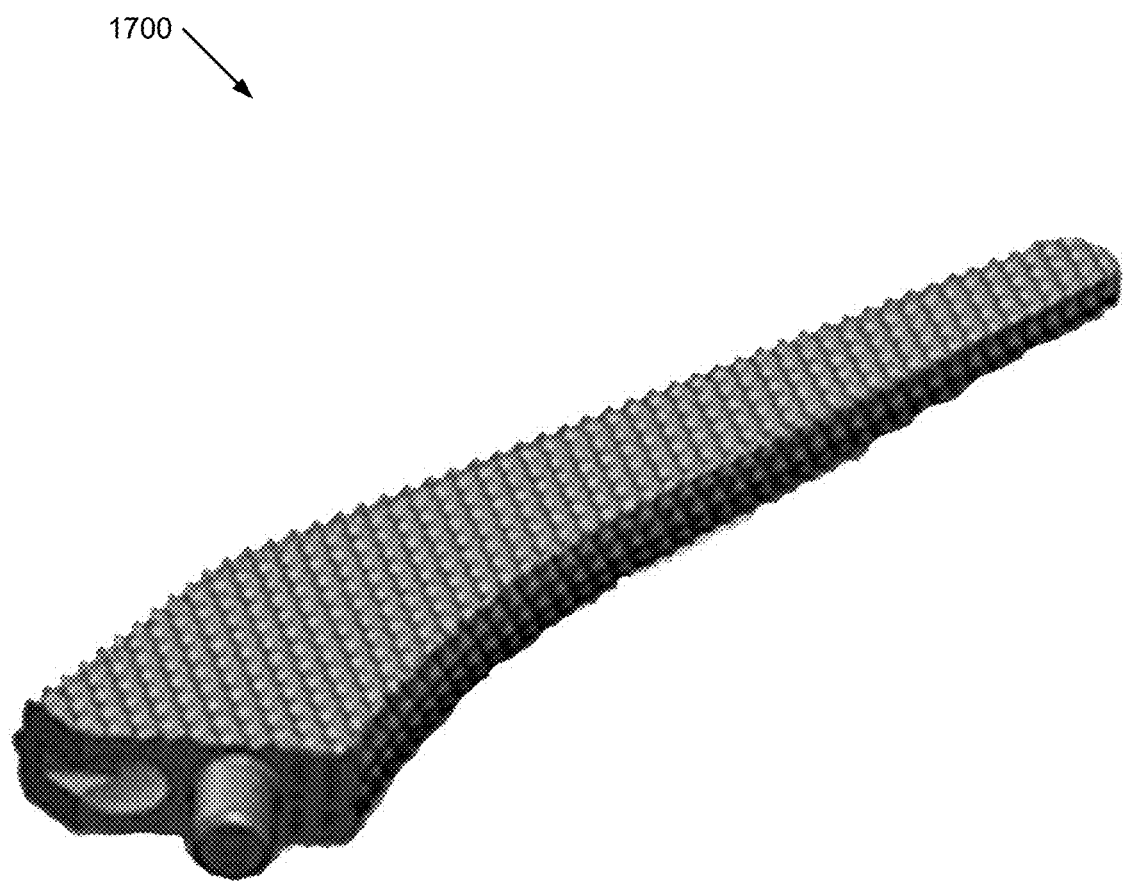
FIG. 17 illustrates an example of a particular bone preparation implement, a broach, which may be used in the present invention.

FIG. 17 illustrates an example of a particular bone preparation implement 1700, a broach, which may be used in the present invention in lieu of, or in addition to, prosthesis P illustrated in FIG. 1, FIG. 10, and FIG. 16. Bone preparation implement P may include the broach, a reamer, a drill, a saw, or other tool, device, or implement for the selective removal of a portion of bone, such as preparation of a cavity for receipt of a prosthesis or an implant or the like.

As noted herein, it may be possible to obtain a quantimetric realtime assessment of a pressfit fixation of an implant during the installation process itself. A goal of some embodiments of the present invention is to estimate, measure, assess, determine and/or establish an assessment (e.g., a quantitative assessment) of pressfit fixation of a prosthesis to be installed into a portion of bone during bone preparation of the cavity itself before the implant is attempted to be installed. That is for example, while reaming a cavity in a hip for an acetabular cup or broaching a channel in a long bone for an implant, it may be helpful if the surgeon were able to estimate, during the bone preparation phase, what the pressfit fixation of the implant into the prepared portion of bone would be based upon parametric evaluation of a bone/implement interface during the preparation.

An incorporated patent application filed on even date as this application discusses and teaches quantitative assessment of pressfit fixation of an cavity/implant interface. Where that application employs an implant or prosthesis, this application employs a bone preparation implement. There may not be a cavity per se, however the bone preparation implement has an applied force F1 such as from a bone preparation agency and there may be one or more assessed forces responsive to that or those forces. These assessed forces may include one or more of an implement-response force F2, an interface-response force F3, and/or a bone-response force F5 in response to operation of the bone preparation implement at a bone-implement interface.

With respect to curves illustrating a response (NOI) to mIF (e.g., FIG. 3) and other response curves for installation of a prosthesis, the same or similar curves may be developed for some embodiments of a bone preparation implement with respect to a portion of bone being prepared for such an implant. The implement may have the same or similar response as FIG. 3-FIG. 9, and FIG. 11-FIG. 14 as the implant and an parametric assessment of the bone preparation implement during bone preparation is anticipated may provide in some embodiments an assessment (quantitative or qualitative for example) of the implant once installed.

When features of the implant to be installed have a predetermined relationship to some or a portion of the bone preparation implement, then an assessment of the implement "fixation" or response at the bone/implement interface during preparation may be used to estimate how that related implant will perform when installed in the prepared bone. For example when a diameter of a reamer forming a cavity generally matches a dimension of a cup to be installed in that cavity or when a broach forming a channel generally matches a dimension of a neck of an implant is installed into that channel, the performance of the bone preparation implement may be used to gauge, estimate, predict, determine, and/or establish what the performance of the implant will or may be once installed.

Other features, such as data variable fusing, and use of a set of sensors (mechanical or biologic, removable or fixed, external or internal, and the like, may be used with the bone preparation implement as described herein with respect to an association with the prosthesis P. A bone preparation implement may be adapted to modifications in an implant, such as a reamer may be provided with a "snub" apex when installing a snubbed acetabular cup as illustrated in FIG. 15. The system 1600 which includes a sensing mechanism for determining one or more responsive forces (including first/second order derivatives of one or more forces) including F2, delta F2, F3, delta F3, F5, delta F5, weighted data fusions, and other responsive forces to a bone preparation agency and/or applied force F1. It may be necessary or desirable to include additional sensing elements, including remote sensors located at a bone/implement interface to measure F3 or located on or in the portion of bone to measure F5 and communicate that sensed information (as part of sensing system 1615) to controller 1620. In some embodiments, the bone preparation implement is assessed the same or similarly as if it were considered to be prosthesis P in some of the discussions herein.

The following references, expressly incorporated by reference hereto in their entireties for all purposes, support one or more of the concepts or ideas presented herein, including: 1) Udomkiat P, Dorr L D, Wan Z. Cementless hemispheric porous-coated sockets implanted with press-fit technique without screws: average ten-year follow-up. J Bone Joint Surg. 2002; 84A:1195; 2) Takedani H, Whiteside L A, White S E, et al. The effect of screws and pegs on cementless acetabular fixation. Trans Orthop Res Soc 1991; 16:523; 3) 1Ahnfelt, L., P. Herberts, H. Malchau, and G. Andersson. Prognosis of total hip replacement: a swedish multicenter study of 4664 revisions. Acta Orthop. Scand. 61:2-26, 1990; 4) Corbett, K. L., E. Losina, A. A. Nti, J. J. Prokopetz, and J. N. Katz. Population-based rates of revision of primary total hip arthroplasty: a systematic review. PLoS ONE 5:e13520, 2010; 5) Huiskes, R. Failed innovation in total hip replacement: diagnosis and proposals for a cure. Acta Orthop. Scand. 64:699-716, 1993; 6) Harris, W. Aseptic loosening in total hip arthroplasty secondary to osteolysis induced by wear debris from titanium-alloy modular femoral heads. JBJS. 73:470-472, 1991; 7) Kobayashi, S., K. Takaoka, N. Saito, and K. Hisa. Factors affecting aseptic failure of fixation after primary charnley total hip arthroplasty multivariate survival analysis. JBJS. 79:1618-1627, 1997; 8) Lombardi Jr, A. V., T. Mallory, B. Vaughn, and P. Drouillard. Aseptic loosening in total hip arthroplasty secondary to osteolysis induced by wear debris from titanium-alloy modular femoral heads. JBJS. 71:1337-1342, 1989; 9) Huiskes, R. Failed innovation in total hip replacement: diagnosis and proposals for a cure. Acta Orthop. Scand. 64:699-716, 1993; 10) Clohisy, J. C., G. Calvert, F. Tull, D. McDonald, and W. J. Maloney. Reasons for revision hip surgery: a retrospective review. Clin. Orthop. Relat. Res. 429:188-192, 2004; 11) Kim, Y. S., J. J. Callaghan, P. B. Ahn, and T. D. Brown. Fracture of the acetabulum during insertion of an oversized hemispherical component. JBJS. 77:111-117, 1995; 12) Sharkey, P. F., W. J. Hozack, J. J. Callaghan, Y. S. Kim, D. J. Berry, A. D. Hanssen, and D. G. LeWallen. Acetabular fracture associated with cementless acetabular component insertion: a report of 13 cases. J. Arthroplast. 14:426-431, 1999; 13) Weeden, S. H. and W. G. Paprosky. Minimal 11-year follow-up of extensively porous-coated stems in femoral revision total hip arthroplasty. J. Arthroplast. 17:134-137, 2002; 14) Ulrich A D, Seyler T M, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 15) Olory, B., E. Havet, A. Gabrion, J. Vernois, and P. Mertl. Comparative in vitro assessment of the primary stability of cementless press-fit acetabular cups. Acta Orthop. Belg. 70:31-37, 2004; 16) Meneghini, R. M., C. Meyer, C. A. Buckley, A. D. Hanssen, and D. G. Lewallen. Mechanical stability of novel highly porous metal acetabular components in revision total hip arthroplasty. J. Arthroplast. 25:337-341, 2010; 17) Fehring, K. A., J. R. Owen, A. A. Kurdin, J. S. Wayne, and W. A. Jiranek. Initial stability of press-fit acetabular components under rotational forces. J. Arthroplast 29:1038-1042, 2014; 18) Georgiou, A., and J. Cunningham. Accurate diagnosis of hip prosthesis loosening using a vibrational technique. Clin. Biomech. 16:315-323, 2001; 19) Balch C M, Freischlag J A, Shanafelt T, Stress and Burnout Among Surgeons. ARCH SURG/VOL 144 (NO. 4) APRIL 2009; 20) Shanafelt T D, Balch C M, Bechamps G J, Tussell T, Dyrbye L, Satele D, Collicott P, Novotny P J, Sloan J, Freischlang J A Burnout and Career Satisfaction Among American Surgeons Ann Surg 2009; 250: 107-115; 21) Ulrich A D, Seyler T M, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 22) Kurtz S, Ong K, Lau E, Mowat F, Halpern M, Projections of Primary and Revision Hip and Knee Arthroplasty in the United States from 2005 to 2030 JBJS (2007) Am 89: 780-785; 23) Nakasone S, Takao M, Nishii T, Sugano N, Incidence and Natural Course of Initial Polar Gaps in Birmingham Hip Resurfacing Cups. J of Arthroplasty Vol 27, (9) 1676-1682; and 24) Springer B D, Griffin W L, Fehring T K, Suarez J, Odum S, Thompson C Incomplete Seating of Press-Fit porous Coated Acetabular Components (2008) J of Arthroplasty Vol 23 (6) 121-126.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An apparatus for preparing a portion of bone for an insertion of a prosthesis, comprising:
    a bone preparation device providing a bone preparation force to the portion of bone using a bone preparation implement engaging the portion of bone, said preparation force operating over a period, said period including an initial preparation act with said preparation device and a subsequent preparation act with said preparation device; and
    a system physically coupled to said preparation device configured to provide a real-time parametric estimation, during said period, of a pressfit fixation of the prosthesis to be installed into the portion of bone, said parametric evaluation including an evaluation of a set of factors of the implement with respect to the portion of bone, said set of factors including one or more of a rigidity factor, an elasticity factor, and a combination of said rigidity factor and said elasticity factor.

2. The apparatus of claim 1 wherein said rigidity factor includes a quantitative assessment of a relative motion of the implement with respect to the portion of bone.

3. The apparatus of claim 2 wherein said elasticity factor includes a quantitative assessment of a time-derivative of said relative motion.

4. The apparatus of claim 2 wherein said preparation force includes a first application of a first preparation force (F1) to the implement and a first determination of a first assessed force response of the implement with respect to the portion of bone.

5. The apparatus of claim 4 and wherein said quantitative assessment includes a first comparison of said first preparation force to said first assessed force response.

6. The apparatus of claim 4 wherein said preparation force includes a second application of said first preparation force to the implement subsequent to said first application of said first preparation force and a second determination of a second assessed force response of the implement with respect to the portion of bone and wherein said quantitative assessment includes a first comparison of said first assessed force response to said second assessed force response.

7. The apparatus of claim 6 wherein said assessed force responses include one or more of a tool-response force (F2), an interface-response force (F3), a bone-response force (F5), and combinations thereof.

8. The apparatus of claim 4 wherein said first assessed force response includes one or more of a tool-response force (F2), an interface-response force (F3), a bone-response force (F5), and combinations thereof.

9. The apparatus of claim 8 wherein said elasticity factor includes a predetermined relationship between particular ones of said forces.

10. The apparatus of claim 9 wherein said predetermined relationship includes one or more comparisons selected from the group consisting of how fast F2 approaches F1, how fast delta F2 approaches 0, how fast F5 approaches F1, how fast delta F5 approaches 0, how fast F3 approaches F1, how fast delta F3 approaches 0 when distal collision becomes elastic (F1 about equal to F2 about equal to F3 about equal to F5), and combinations thereof.

11. The apparatus of claim 10 wherein said rigidity factor includes a predetermined relationship between particular ones of said forces.

12. The apparatus of claim 11 wherein said predetermined relationship includes one or more comparisons selected from the group consisting of when F2 approaches F1, when delta F2 approaches 0, when F5 approaches F1, when delta F5 approaches 0, when F3 approaches F1, when delta F3 approaches 0 when distal collision becomes elastic (F1 about equal to F2 about equal to F3 about equal to F5, and combinations thereof).

13. The apparatus of claim 8 wherein said rigidity factor includes a predetermined relationship between particular ones of said forces.

14. The apparatus of claim 13 wherein said predetermined relationship includes one or more comparisons selected from the group consisting of when F2 approaches F1, when delta F2 approaches 0, when F5 approaches F1, when delta F5 approaches 0, when F3 approaches F1, when delta F3 approaches 0 when distal collision becomes elastic (F1 about equal to F2 about equal to F3 about equal to F5, and combinations thereof).

15. The apparatus of claim 8 further comprising, for each combination of forces, a set of corresponding sensors including one or more of an F1 sensor, an F2 sensor, an optional F3 sensor, and an optional F5 sensor, said set of corresponding sensors configured for said real-time production of said corresponding force(s) during said period.

16. The apparatus of claim 1 wherein said elasticity factor includes a quantitative assessment of a time-derivative of a relative motion of the implement with respect to the portion of bone.

17. The apparatus of claim 1 wherein said bone preparation implement includes a broach.

18. The apparatus of claim 1 wherein said bone preparation implement includes a reamer.

19. An apparatus for preparing a portion of bone using a bone preparation implement for installing a prosthesis into the portion of a bone, comprising:
- a force applicator operating a bone preparation force configured for a preparation of the portion of bone;
- a force transfer structure, coupled to said force applicator and to the implement, for conveying an application force F1 to the implement, said application force F1 derived from said preparation force;
- a force sensing system determining a force response of the implement at an interface of the implement and the portion of bone, said force response responsive to said application force F1 and a force response component F2; and
- a controller, coupled to force applicator and to said force sensing system, said controller setting an operational parameter for said preparation force, said operational parameter establishing said application force F1, said controller responsive to said force response to establish a set of parameters including one or more of a rigidity metric, an elasticity metric, and combinations thereof;
- further including an F1 sensor and an F2 sensor, both sensors disposed between said force applicator and the implement;
- wherein said application force F1 is measured in real-time by said F1 sensor;
- wherein said force response component is measured in real-time by said F2 sensor.

20. The apparatus of claim 19 wherein the implement includes a broach.

21. The apparatus of claim 19 wherein the implement includes a reamer.

22. An apparatus for preparing a portion of bone using a bone preparation implement for installing a prosthesis into the portion of a bone, comprising:
- means for applying a bone preparation force to the implement, said preparation force operating over a period, said period including an initial preparation act with a bone preparation device and a subsequent preparation act with said bone preparation device; and
- means, physically coupled to said bone preparation device, for estimating a pressfit fixation of the prosthesis once installed into the portion of bone after preparation during said period, said estimation including an evaluation of a set of factors of the implement with respect to the portion of bone, said set of factors including one or more of a rigidity factor, an elasticity factor, and a combination of said rigidity factor and said elasticity factor.

23. The apparatus of claim 22 wherein said set of factors includes both said elasticity factor and said rigidity factor, further comprising:
- means, responsive to said factors, for modifying periodically said preparation force to automatically prepare the portion of bone to provide a cavity for the prosthesis that when the prosthesis is installed within said cavity it may be installed at a best fixation short of fracture.

24. The apparatus of claim 22 wherein the implement includes a broach.

25. The apparatus of claim 22 wherein the implement includes a reamer.

* * * * *